United States Patent
De Wit et al.

(10) Patent No.: US 8,277,814 B2
(45) Date of Patent: Oct. 2, 2012

(54) AVIAN ASTROVIRUS

(75) Inventors: Sjaak De Wit, Deventer (NL); Carla Christina Schrier, Boxmeer (NL); Marcel Van de Laar, Boxmeer (NL); Iwan Verstegen, Boxmeer (NL)

(73) Assignee: Intervet International B.V., Boxmeer (NL)

( * ) Notice: Subject to any disclaimer, the term of this patent is extended or adjusted under 35 U.S.C. 154(b) by 0 days.

(21) Appl. No.: 12/989,865

(22) PCT Filed: Apr. 27, 2009

(86) PCT No.: PCT/EP2009/055036
§ 371 (c)(1),
(2), (4) Date: Oct. 27, 2010

(87) PCT Pub. No.: WO2009/133054
PCT Pub. Date: Nov. 5, 2009

(65) Prior Publication Data
US 2011/0104178 A1  May 5, 2011

Related U.S. Application Data

(60) Provisional application No. 61/048,751, filed on Apr. 29, 2008.

(30) Foreign Application Priority Data

Apr. 28, 2008 (EP) .................................. 08155271

(51) Int. Cl.
*A61K 39/12* (2006.01)
*A61K 38/00* (2006.01)
(52) U.S. Cl. .................................. 424/185.1; 424/93.3
(58) Field of Classification Search .................. None
See application file for complete search history.

(56) References Cited

U.S. PATENT DOCUMENTS
2009/0092634 A1 * 4/2009 Todd et al. .............. 424/199.1

FOREIGN PATENT DOCUMENTS

| EP | 382271 | 12/1994 |
|---|---|---|
| EP | 1140152 | 8/2003 |
| WO | WO 2004/027053 | 4/2004 |
| WO | WO 2007/077464 | 7/2007 |

OTHER PUBLICATIONS

Baxendale et al, The isolation and characterisation of astroviruses from chickens, 2004, Avian Pathology 33:364-370.*
Baxendale et al, "The Isolation and Characterisation of Astroviruses from Chickens", Avian Pathology, vol. 33, No. 3, pp. 364-370 (2004) [Abstract].
Bovarnik et al, "The Influence of Certain Salts, Amino Acids, Sugars, and Proteins on the Stability of Rickettsiae", Journal of Bacteriology, vol. 59, pp. 509-522 (1950).
Imada et al, "Avian Nephritis Virus (ANV) as a New Member of the Family *Astroviridae* and Construction of Infectious ANV cDNA", Journal of Virology, The American Society for Microbiology, US, vol. 74, No. 18, pp. 8487-8493 (2000).
Jiang et al, "RNA Sequence of Astrovirus: Distinctive Genomic Organization and a Putative Retrovirus-Like Ribosomal Frameshifting Signal That Directs the Viral Replicase Synthesis", PNAS-USA, vol. 90, pp. 10539-10543 (1993).
Jonassen et al, "Complete Genomic Sequences of Astroviruses from Sheep and Turkey: Comparison with Related Viruses", Virus Research, vol. 91, pp. 195-201 (2003).
Kawaguchi et al, "Establishment and Characterization of a Chicken Hepatocellular Carcinoma Cell Line, LMH", Cancer Research, vol. 47, pp. 4460-4464 (1987).
Koci et al, "Molecular Characterization of an Avian Astrovirus", Journal of Virology, vol. 74, No. 13, pp. 6173-6177 (2000).
Koci et al, "Avian Astroviruses", Avian Pathology, vol. 31, No. 3, pp. 213-227 (2002) [Abstract].
Koci, "Review: Immunity and Resistance to Astrovirus Infection", Viral Immunology, vol. 18, pp. 11-16 (2005).
Moser et al, "Review: Pathogenesis of Astrovirus Infection", Viral Immunology, vol. 18, pp. 4-10 (2005).
International Search Report for corresponding PCT/EP2009/055036 mailed on Aug. 10, 2009.

* cited by examiner

*Primary Examiner* — Bao Li

(57) ABSTRACT

The present invention relates to the fields of veterinary virology and immunology. In particular the invention relates to a novel avian Astrovirus; to antibodies or fragments thereof against the novel virus; to antigenic preparations, proteins, and DNA molecules of the novel avian Astrovirus; to vaccines of the novel virus or its antigenic preparations, protein, or DNA; to methods for the manufacture of such vaccines, and to diagnostic kits.

14 Claims, 6 Drawing Sheets

FIG. 1

Figure 3:
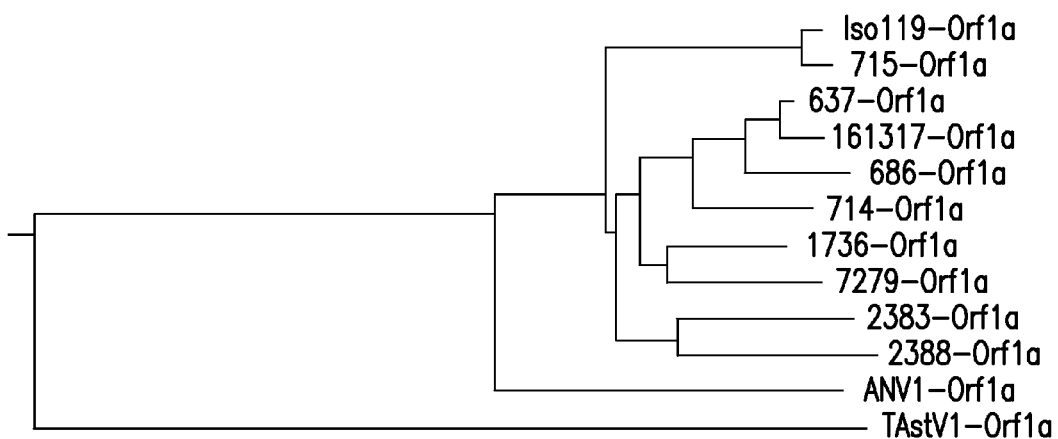

```
Isolate19-Orf1a  241 GACCTTGAAGATCGAGGAGAATGGTATGGCCAGTCTGGGAAACCTAGGAGGATAACCTTT
637-Orf1a        241 .........................T......AC.................C
686-Orf1a        241 ..T.....C......T................AC.................C
714-Orf1a        241 ..............C........T....C..TC..................C
715-Orf1a        241 ...........................T.........................
1736-Orf1a       241 ..T.....G........C..............TC....................
2383-Orf1a       241 ..T......T.....G.....T......A...T.......A........C
2388-Orf1a       241 AGT........T..C..C..............A..G........A........C
7279-Orf1a       241 ..T..........T..C...............TC...............T...
161317-Orf1a     241 .................T..............AC..................C
ANV1-Orf1a      2453 .....C..G...A....T......T...------------.....AA.......C Isolate19-Orf1a  301 AAACAGAGAGCGATGCTTCGCTTCATTCAGCTTGGTCGACAACAACAAATAGCCACAATT
637-Orf1a        301 ..G..A..G............A.....C..A.............C..........
686-Orf1a        301 .....A..G..........T.....C..A.........G.....C..........
714-Orf1a        301 ..G........T........T..C..A..........G......C..........
715-Orf1a        301 ..G...........G..........................................
1736-Orf1a       301 ..G....................A.....G..............C...T......
2383-Orf1a       301 ..GG.A................T...............G.....T.CG.....T..C
2388-Orf1a       301 ..GG.A.................A..C..GA..........................
7279-Orf1a       301 ..G.....G..A.............C..G..............CG...........
161317-Orf1a     301 ..G..A..G............A.....C..A.............C..........
ANV1-Orf1a      2501 ..G..A...........T........A.....C..G........GG.G.....TG.C Isolate19-Orf1a  361 TCATTTCCTGATGGCTATGAAGATAGAGCTGAAGAACTCTATAATAA
637-Orf1a        361 ..............................G......T......
686-Orf1a        361 ..............................G..G...T...C..
714-Orf1a        361 .................................G..........
715-Orf1a        361 .............................................
1736-Orf1a       361 ...C........T...................T.T...C..
2383-Orf1a       361 .....C..A....T..................T.........
2388-Orf1a       361 .......C.....T.G................A...T...C..
7279-Orf1a       361 ............T.....................TC..C..
161317-Orf1a     361 ..............................G......T......
ANV1-Orf1a      2561 ............T.....G..C.................C.....
```

FIG.1-1

```
Isolate19   1 TKSISKAAFMKTKVLTEEEYRRLEEEGFSKDEIKEIVDNLREQAWIDYQ
637         1 ................................................
686         1 ................................................
714         1 ................................................
715         1 ................................................
1736        1 ................................................
2383        1 ................................................
2388        1 ............................R...................
7279        1 ..A..............................................
161317      1 ................................................
ANV1        1 ..A.....................T....D..........L...

Isolate19  50 NQLDEEGDDDWYEQMTEDQRINDEIDKQIEQDLEDRGEWYGQ SGKP R
637        50 .........................................D.... ..Q. .
686        50 .........................................D.... ..Q. .
714        50 .........................................D.... ..Q. .
715        50 ............................................ ...S .
1736       50 .........................................D.... ..Q. .
2383       50 ...............V......R....................... ...L .
2388       50 ...............V......R....S....D.............. .... .
7279       50 .........................................D.... ..Q. .
161317     50 .........................................D.... ..Q. .
ANV1       50 ...............E.......Q..QN..R................ ---- .

Isolate19  97 RITFKQRAMLRFIQLGRQQQIATISFPDGYEDRAEELYN
637        97 ....................T.................F.
686        97 ....................T.................F.
714        97 ....................T....................
715        97 .........................................
1736       97 ....................T....L............F.
2383       97 .....E..........HT.....................F.
2388       97 .....E....................C......IF.
7279       97 ....................T.................F.
161317     97 ....................T.................F.
ANV1       95 K...................V..V.................
```

FIG.2

```
ANV1-Orf1a   2213  ACCAAAGCGATCTCTAAGGCTGCCTTCATGAAAACTAAAGTCCTCACCGA
Isol19-Orf1a    1  ..T...T.......A..A................A.........T.....
                                                     |       >/
                                                             primer ANV1-Orf1a   2263  AGAAGAATATCGCCGGTTAGAGGAGGAAGGCTTCACTAAAGATGAGATCA
Isol19-Orf1a   51  .........C..T............A.........T.A...........T.
                   /――――――>|
                   SEQ ID NO 30

ANV1-Orf1a   2313  AGGACATCGTTGACAATCTCAGAGAGCAGGCGTGGCTCGACTATCAGAAC
Isol19-Orf1a  101  .A..G.....G........GC....A..A..C...A....T..C.....T ANV1-Orf1a   2363  CAACTTGATGAAGAAGGTGATGATGACTGGTACGAACAAATGGAAGAGGA
Isol19-Orf1a  151  ...G..A.....................T..G......ACT..A..

ANV1-Orf1a   2413  TCAAAGAATTAATGATCAAATTGACCAAAACATTGAAAGAGACCTCGAGG
Isol19-Orf1a  201  ................G.G.....TA.GC.A.....GCA......T..A.

2485          2486
                                          |             |
ANV1-Orf1a   2463  ATAGAGGTGAATGGTATGGTCAG------------AGGAAAATAACCTTC
Isol19-Orf1a  251  ..C.....A...........C...TCTGGGAAACCT....GG........T
                                          |<――――――――――――|
                                            primer SEQ ID NO: 31

ANV1-Orf1a   2501  AAGCAAAGAGCGATGCTTCGTTTCATTCAACTTGGCCGGCAACAACAGGT
Isol19-Orf1a  301  ...A..G..............C........G.....T..A.........AA.

ANV1-Orf1a   2551  GGCCACTGTCTCATTTCCTGATGGTTATGAGGACAGAGCTGAAGAACTCT
Isol19-Orf1a  351  A.....AA.T...............C......A..T................

ANV1-Orf1a   2601  ACAATAA
Isol19-Orf1a  401  .T.....
```

FIG.4

AVIAN ASTROVIRUS

RELATED APPLICATIONS

This application is a national stage entry under 35 U.S.C. §371 of PCT/EP2009/055036 filed on Apr. 27, 2009, which claims priority to U.S. Provisional Application No. 61/048,751 filed on Apr. 29, 2008 and EP Application No. 08155271.3 filed on Apr. 28, 2008.

The present invention relates to the fields of veterinary virology and immunology. In particular the invention relates to a novel avian Astrovirus; to antibodies or fragments thereof against the novel virus; to antigenic preparations, proteins, and DNA molecules of the novel avian Astrovirus; to vaccines of the novel virus or its antigenic preparations, protein, or DNA; to methods for the manufacture of such vaccines, and to diagnostic kits.

Astroviruses are small, round, non-enveloped viruses having a single stranded RNA genome of positive sense. Most Astroviruses have been associated with causing some sort of enteritis, giving rise to diarrhoea, vomiting, malabsorbtion, general malaise, and growth retardation. Infection can be lethal in humans or animals that are less resilient, such as young, old, or immunocompromised individuals. See: Matsui and Greenberg (in: Fields virology, $3^{rd}$ ed., 1996, ed.: B. Fields et al., ISBN: 781702534, chapter 26), and: Moser and Schultz-Cherry (2005, Viral Immunology, vol. 18, p. 4-10).

Also, the severity of Astrovirus induced pathology can vary resulting from differences in virulence between Astrovirus species or strains themselves. This has created the belief that some of the Astroviruses act as secondary pathogens, which by themselves cause only a sub-clinical disease, while full clinical symptoms of disease are only manifested when there is an additional cause of disease from another pathogen.

The mechanism by which immunity against Astrovirus infection is achieved is also not completely clear; virus-neutralising antibodies do seem to play a part in defence and immunological memory, but are probably not the only effectors of an immunerespons against Astrovirus infection. This is reviewed by M. Koci (2005, Viral Immunology, vol. 18, p. 11-16).

Astroviruses have been detected worldwide and were isolated from a wide variety of animals. In turn, amongst the Astrovirus species infecting a certain target animal, several serotypes have been described. Taxonomically the Astroviridae family is divided into two main genuses, the mammalian Astroviruses: Mamastrovirus, and the avian Astroviruses: Avastrovirus. At the moment the genus Avastrovirus comprises the formally recognized species: Avian Nepritis Virus 1 and 2 (ANV1, 2) (from chickens), and Turkey Astrovirus 1 and 2 (TAstV1, 2).

Several additional avian Astroviruses have been isolated from duck, chicken, ostrich and turkey. For instance, chicken astrovirus 2 (CAstV2) has been described by Baxendale and Mebatsion (2004, Avian pathology, vol. 33, p. 364-370; and in international patent application WO 2004/027053), and Todd et al. described a CAstV3 (WO 2007/077464), which is closely related to CAstV2. These Astroviruses have not yet been formally classified, as reviewed by Koci and Schulz-Cherry (2002, Avian Pathology vol. 31, p. 213-227).

Astroviruses are very stable in the environment, e.g. they can resist common lipid-solvents and detergents, have a wide pH tolerance, and are comparatively thermostable. This, combined with their high infectivity and easy transmission by faecal-oral route, explains why Astroviruses or antibodies against them can be found in so many humans and animals worldwide.

The classification and naming of these small RNA viruses has been subject to frequent change, when updating was required to fit new experimental data. For instance: the duck Astrovirus (DAstV) was formerly classified as a Picorna virus, and was originally called duck hepatitis virus type II, as it causes hepatitis. Similarly, ANV1 was formerly described as a Picornavirus, in particular an Enterovirus, but was re-classified to the Avastroviruses (Imada et al., 2000, J. of Virology, vol. 74, p. 8487-8493). ANV1 is also called: chicken Astrovirus 1 (CAstV1), and causes nephritis.

Re-classification of these viruses was called for upon the availability of new information on the sequence and organisation of their viral genome. Particularly for Astroviridae, it was shown that physical, electron-microscopic, and biochemical characterisations often do not suffice to differentiate the Astroviridae from other so-called "small round viruses", or "enterovirus-like viruses" such as Picorna-, Calici-, or Hepeviridae (Hepatitis E like viruses), or even from enveloped RNA viruses such as Reo-, Rota-, or Coronaviruses which cause disease symptoms much resembling those of Astroviruses. This is because the results of such characterisations vary with the method and the conditions used. Therefore these are not consistent enough to make the right determination.

On the other hand, molecular biological characterisation such as genotyping, in combination with immunologic characterisation is detailed and reproducible enough to assign a micro-organism to the proper taxonomic group (Van Regenmortel et al., 2000, in: Virus Taxonomy, $7^{th}$ report of the ICTV, Academic press, New York). Therefore ideally such determinations are based on nucleotide sequencing, polymerase chain reaction (PCR) assays, and serological typing assays.

The RNA genome of the Astroviridae is roughly about 7 kb in size, with a genome organisation that is typical for this virus family, see: Jiang et al. (1993, PNAS-USA, vol. 90, p. 10539-10543) and Koci et al. (2000, J. of Virology, vol. 74, p. 6173-6177). According to current understanding, the genome incorporates three clearly recognisable open reading frames (ORF's), from 5' to 3':

ORF 1a: is about 3 kb in size, encodes a non-structural protein having a serine protease motif.
ORF 1b: is about 1.5 kb in size, partly overlaps with ORF 1a, and encodes a non-structural RNA-dependent RNA polymerase.
ORF 2: encodes the structural viral proteins, via a sub-genomic RNA of about 2 kb. The expresssed polyprotein is probably cleaved into smaller parts before viral assembly, and comprises a.o. the capsid- or coat protein.

Of the three ORF's, ORF 1b has the most conserved nucleotide sequence as compared among the Astrovirus nucleotide sequences that are publicly available, and ORF 2 is the ORF most variable in sequence.

Some particular disease problems were observed between 1987 and today, in poultry operations in the Netherlands, Germany and United Arab Emirates, with chickens and turkeys suffering from diarrhoea, reduction in feed conversion and growth, as well as from problems with swelling and painfulness of the joints and tendons of the legs. These problems were found in broiler-, breeder-, and layer type birds, of various ages, and at different farms having no apparent mutual connection.

Lameness was observed in birds in their first week of age, up until several months of age. Animals presented swollen hock (ankle) joints and tendon-shafts of the lower leg, both overfilled with a clear, slightly viscous liquid, and symptoms of arthritis. A reduction of the feed utilization and growth rate was observed in these birds, most likely as result of the locomotory problems. In the worst cases the birds were no longer able to move and thereby get feed or drink, resulting in mortality. These leg abnormalities were most prominent in the heavier broiler-type birds, however the economic damage sustained was considerable in all types of birds.

Even more impact had the diarrhoea that was observed, mainly in younger birds, but also in birds of egg-laying age. Symptoms varied from indigestion to clear enteritis, and resulted in reduction of feed conversion; growth depresssion or even weight loss; drop in egg production ("egg-drop"); increase in the numbers of eggs of poor quality; and mortality.

On some farms the problems were observed over several years, resulting in sustained bad production figures without definite cause.

Upon post mortem investigations, in several instances body parts other than intestines or leg joints were also found to be affected, such as displayed by erosion of the gizzard or swelling of the liver.

To detect the cause for these symptoms, aspects of management and diet were investigated but these could not be linked to the problems observed in these cases. Also pathogens were investigated that could be responsible, in particular an infection by Reovirus, as this virus is well known for causing malabsorbtion and joint problems. However, in spite of the use of a variety of assays, in many cases no Reovirus could be detected.

Several other pathogens were also investigated either routinely or specifically for being known to cause similar problems, such as the bacteria: *Salmonella, Mycoplasma, Haemophilus*, and *Pasteurella*; and the viruses: Adenovirus, Infectious Bronchitis virus (IBV), Newcastle Disease virus (NDV), Infectious Bursal Disease virus (IBDV), Egg Drop Syndrome (EDS), and Avian Influenza virus (AIV).

Up until today, no causative agent could be linked to the leg- and intestinal problems that were observed, in spite of the severity, the problems for the animal's welfare, and the resulting bad economic performance of these poultry operations.

Consequently a need exists to identify an agent connected to the disease-symptoms observed and to provide vaccines and diagnostics, which provide prevention of the disease and identification of the causative agent.

Surprisingly a new virus has been found in chickens and turkeys suffering from intestinal and locomotory disease. The virus could be isolated from diseased birds of various ages, types, and origins, both from joints and tendons as well as from various internal organs. The isolated virus in turn induced similar symptoms of disease upon infection of healthy test animals, and could be re-isolated from the diseased test animals, thereby fulfilling Koch's postulates.

The new virus can be used to develop diagnostic assays and vaccines to detect and to combat the virus and the disease problems it causes in poultry, in particular disease of joints and tendons as well as of the gastro-intestinal tract.

The novel virus was analysed in a number of ways, and was surprisingly identified as an Astrovirus. Because of its prevalence in chickens and turkeys it is tentatively qualified as an avian Astrovirus.

Among many other characterisations, the fact that the new virus as described herein is non-enveloped followed from the results of two consecutive extractions with chloroform, after which the extracted virus sample still was able to cause a specific pathogenic effect in embryonated chicken SPF eggs.

The presence of an RNA genome in the new virus followed from the fact that useable nucleic acid for further analysis could only be obtained after RNA extraction and RT-PCR, not after DNA isolation and regular PCR.

Surprisingly, the closest (yet distinguishable) relatives were found to be ANV1 type viruses, therefore the novel avian Astroviruses described herein represent a novel group of avian nephritis viruses, tentatively classified as ANV3 viruses.

However the inventors have surprisingly found a number of features that distinguishes the novel avian Astroviruses described herein from ANV1 and other (Astro-) viruses, and uniquely characterises the different isolates of the novel avian Astrovirus as belonging to a novel and separate group of its own.

The main characterising feature relates to the presence of a specific nucleotide sequence which is identifyable by nucleotide sequence analysis and by PCR assay.

Distinct pathologic symptoms induced upon infection of embryos were also observed. Specific immunological differences were detectable by serotyping using VN- or IFT-assays. All these will be described below with experimental results and -details.

The invention relates to an isolated novel avian Astrovirus having an open reading frame (ORF) 1a genomic region, characterised in that the ORF1a of said avian Astrovirus, when compared to the ORF 1a of avian nephritis virus 1, contains an insert of 12 nucleotides, said insert being located in between nucleotides corresponding to the nucleotides numbered 2485 and 2486 of SEQ ID NO: 1.

Preferred "avian" organisms are poultry; more preferred avian organisms are selected from the group consisting of chicken, turkey, duck and goose. Most preferred is chicken.

The term "Astrovirus" indicates the relationship of the group of new viruses according to the invention to viruses that are currently described and/or classified as belonging to the taxonomic family of the Astrovirideae. However, the skilled person will realise that such taxonomic classification may change over time as new insights could lead to reclassification into new or other taxonomic groups. However, as this does not alter the characteristics of the virus according to the invention but only its classification, such re-classified organisms remain to be within the scope of the invention.

In particular the invention encompasses all viruses subclassified from the avian Astrovirus according to the invention into a sub-species, strain, isolate, genotype, serotype, variant or subtype and the like.

Therefore, for the invention, an "Astrovirus" is a virus having the characterising features of a virus classified as an Astrovirus. Such characterising features relate e.g. to molecular, bio-chemical, and biological features; for instance to having a positive sense single stranded RNA genome comprising ORF's identifiable as 1a, 1b and 2; being a non-enveloped virion of about 28-30 nm; and causing an enteritis.

The term "genomic region" is meant to indicate a part of the genetic material of the novel avian Astrovirus according to the invention. Such a region will consist of nucleic acid; in the case of the novel avian Astrovirus according to the invention, the nucleic acid is RNA.

The genome of the novel avian Astrovirus according to the invention comprises, as do all other Astrovirideae, regions recognisable as and corresponding to ORF's 1a, 1b and 2.

However, it was surprisingly found that the novel avian Astrovirus has some nucleotides in its ORF 1a genomic region which are not present in the ORF 1a of ANV1 or of any other type of (avian) Astrovirus. These nucleotides are present in the form of a linear and continuous stretch of 12 nucleotides, and when compared to the ORF 1a sequence of ANV1 represent an insert into this region. The 12 nucleotide "insert" was present in the ORF 1a of all the isolates tested of the group of novel avian Astroviruses described herein.

The location where the 12 nucleotide insert is present in the ORF 1a of the isolates of the novel avian Astroviruses described herein, is indicated by reference to the numbering as described for the genomic sequence of the reference ANV1 strain, which was described by Imada et al. (2000, J. of Virology, vol. 74, p. 8487-8493). The cDNA sequence of the genomic sequence of this ANV1 strain is also available from the internet nucleotide-database of the American National Institutes of Health, known as Gen Bank, under accession number: AB033998, and is represented herein as SEQ ID NO: 1.

For all isolates of the novel avian Astroviruses according to the invention, the 12 nucleotide insert in ORF 1a was located in between nucleotides corresponding to the nucleotides numbered 2485 and 2486 of SEQ ID NO: 1.

At present it is not known if, or how, this 12 nucleotide insert in ORF 1a of the novel avian Astrovirus according to the invention, which is not present in ORF 1a of ANV1, influences the behavior of this novel avian Astrovirus. Without being bound to any theory, the inventors assume that the fact that the insert exist of 12 nucleotides, thus 4 triplets which keeps the translational frame of ORF1a intact, makes that the encoded 4 additional amino acids are incorporated in the non-structural proteins that are expressed from ORF 1a. It is very well possible that this influences the viruses' pathobiological behaviour, for instance its virulence and its capacity to cause disease of the intestine as well as of legs, joints and tendons.

Nevertheless, the fact that these 12 nucleotides are present in the ORF 1a genomic region of the novel avian Astroviruses described herein, but not in the ORF 1a of ANV1 or other (avian) Astroviruses, provides a positive genetic marker for this novel group of viruses.

As is well known in the art, a genetic marker is a feature of an organisms' genetic material, situated at a certain genomic location, that is useful for making a certain distinction or correlation, and is detectable by technical means. When—as in this case—a feature is present in a group to be identified, it is a "positive" genetic marker for that group.

The nucleotide sequence of the 12 nucleotide insert that characterises the novel avian Astrovirus according to the invention, is not identical for all the isolates of the novel avian Astrovirus described herein, however size and location were identical. The consensus of the nucleotide sequence of the 12 nucleotide insert is:

5'-TCYGGDMARYYT-3', represented herein as SEQ ID NO: 2.

Therefore, in a preferred embodiment the invention is characterised in that the insert of 12 nucleotides has a nucleic acid sequence as presented in SEQ ID NO: 2.

The skilled person will know that the sequence of SEQ ID NO: 2 is a so-called 'denatured' primer sequence, indicating that there are positions (here: the Y, D, M, and R), where one of a number of nucleotides can be present. The commonly used code for indicating denatured bases is the IUPAC code (published in Biochem. J., 1985, vol. 229, p. 281-286), wherein: R=G or A; Y=T or C; M=A or C; K=G or T; S=G or C; W=A or T; H=A, C, or T; B=G, T, or C; V=G, C, or A; D=G, A, or T; and N=G, A, T, or C.

For the novel avian Astrovirus described herein, the presence of this detectable genetic marker allows for the identification of the novel virus and its novel group by detection for instance via DNA sequencing or PCR.

DNA sequencing is a well known technique; standard protocols and equipment for instance for high speed automated sequencing are widely available. Most commonly such protocols employ PCR based "cycle-sequencing", followed by high-definition electrophoresis.

For the nucleic acid sequencing of RNA viruses such as Astroviridae, the nucleic acid to be investigated needs to be in the form of copy DNA (cDNA), as RNA sequencing is not yet feasible. For the preparation of cDNA many standard protocols and commercial kits are available. Such protocols employ a reverse transcriptase enzyme. Commonly a primer is used to initiate the copying process.

An example of a suitable primer for the RT reaction is the DNA oligonucleotide presented herein as SEQ ID NO: 3, being: 5'-TCG WTS CTA CYC-3'. The inventors refer to this primer as primer 17.

This primer hybridises to the far 3' region of the genome of many avian Astroviruses, starting at the nucleotide corresponding to nucleotide number 6731 of SEQ ID NO: 1, and proceeding in reverse direction.

In FIG. 1 is displayed a multiple alignment of the cDNA sequence of a section of ORF 1a from a selected number of isolates of the avian Astroviruses according to the invention. These are aligned to the corresponding part of the genome of an ANV1 reference virus, as represented in SEQ ID NO: 1. As is clearly visible in the boxed area, all isolates possess a 12 nucleotide region, which is not present in the ANV1 ORF 1a. The SEQ ID NO's of the ORF 1a cDNA sequence of the isolates of the avian Astrovirus according to the invention are listed in Table 1.

Similarly, FIG. 2 displays a multiple alignment of the putative amino acid sequences, as prepared by computer translation of the cDNA sequences listed in FIG. 1. As is visible in the boxed area, the protein encoded by ORF 1a of the avian Astroviruses according to the invention contains 4 amino acids, that are not present in the protein encoded by ORF 1a of ANV1. The SEQ ID NO's of the translated ORF 1a sequence of the isolates of the avian Astrovirus according to the invention are listed in Table 1.

With respect to the isolates of the avian Astroviruses according to the invention: a large number of field isolates were collected over time from chickens and turkeys suffering from leg and/or intestinal disease as described above. Of these isolates many were analysed, which led to the invention of the novel group of avian Astroviruses as described herein. However, only a selection of all analysed isolates are presented herein, to define the novel avian Astrovirus in the context of the natural variation occurring in that group.

Table 1 presents a description of the isolates of the avian Astrovirus according to the invention, that are described herein. Also Table 1 lists the SEQ ID NO's of the cDNA and putative protein sequences from ORFs 1a, 1b and 2 from a selection of isolates.

TABLE 1

Characteristics of a selection of isolates of the avian Astrovirus according to the invention; also SEQ ID NO's of sequenced cDNA regions ("nt") and putative encoded proteins ("aa").

| | Donor animal: | | | | SEQ ID NO's | | |
|---|---|---|---|---|---|---|---|
| Isolate number | species | type | age | tissue | Orf 1a | Orf 1b | Orf 2 |
| 161319 "Isolate 19" | Chicken | layer | 36 w | Trachea | nt: 4<br>aa: 5 | nt: 6<br>aa: 7 | nt: 8<br>aa: 9 |
| 637 | Chicken | broiler | 12 d | Tendon and hock-cartilage | nt: 10<br>aa: 11 | | |
| 686 | Chicken | broiler | 10 d | Various organs | nt: 12<br>aa: 13 | | |
| 714 | Chicken | broiler | 30 d | Ceacal tonsils and pancreas | nt: 14<br>aa: 15 | | |
| 715 | Chicken | broiler | 30 d | Ceacal tonsils and pancreas | nt: 16<br>aa: 17 | | |
| 1736 | Chicken | broiler | — | Tendon and tibia | nt: 18<br>aa: 19 | | |
| 2383 | Turkey | broiler | — | Joint and synovial fluid | nt: 20<br>aa: 21 | | |
| 2388 | Turkey | broiler | — | Tendon and tibia | nt: 22<br>aa: 23 | | |
| 7279 | Chicken | — | — | Pancreas | nt: 24<br>aa: 25 | | |
| 161317 | Chicken | layer | 36 w | Trachea | nt: 26<br>aa: 27 | | |

"nt" = nucleotide sequence;
"aa" = amino acid sequence;
"—" = not known

An isolate of the avian Astroviruses according to the invention can be obtained from birds suffering from intestinal or leg-problems by taking a sample from one or more organs, or from joints or tendons of the legs. The samples can be homogenised when required, and for instance be mixed with an appropriate buffer solution, preferably containing antibiotics.

To amplify the viral titre of such isolates, different substrates can be used, such as avian cell-lines or embryonised avian eggs. When using eggs, the suspension can be inoculated into and cultured in embryonated avian eggs. Different inoculation routes are possible, such as on the chorio-allantoic membrane (CAM), or into the yolk sac, or the allantoic fluid cavity. Preferably, the first few rounds of inoculation are into the yolk sac, and later ones (if required) can be into the allantoic fluid. About 5-7 days old, embryonated chicken SPF eggs can be used. Such techniques are all well known to persons skilled in the art, and SPF chicken eggs of appropriate quality and age are commercially available, for instance from Spafas®, or Lohmann®.

After incubation for 2-7 days under appropriate conditions, the embryo, the CAM, or (preferably) the allantoic fluid can be harvested. If required further rounds of amplification on eggs can be performed, by inoculation into the yolk sac or the allantoic fluid. Finally allantoic fluid can be harvested containing high amounts of the avian Astrovirus according to the invention.

For PCR-sequencing of both strands of a representative part of ORF 1a the following primers can conveniently be used:

```
SEQ ID NO: 28:
5'-AAA GGK AAG ACD AAG ARR RAC MG-3',
and

SEQ ID NO: 29:
5'-TCG CCT TCT GGA AGG TCT TCA-3'.
```

The inventors refer to these sequencing-primers as primers F-II and R-II-3 respectively. SEQ ID NO: 28 hybridises starting at nucleotides corresponding to nt 2171 and further of ANV1 (SEQ ID NO:1); SEQ ID NO: 29 hybridises to nucleotides starting at nt 2640 of SEQ ID NO: 1, and proceeding in reverse direction (see Table 4). This way the genome region of ORF 1a of the avian Astrovirus according to the invention comprising the 12 nucleotides not present in ANV1, is covered by the part of ORF 1a that is sequenced.

For computer analyses of the DNA sequences determined, these are trimmed so that they do not contain the denatured sequences from the primers themselves. Also the sequences compared need to be of equal length to achieve representative alignments. Also, the alignments are to be made over the full length of the trimmed sequences. That means for instance in the case of using the primers SEQ ID NO: 28 and 29, that the sequence length to be compared is about 400-425 nucleotides.

A convenient computer program for such manipulations and alignments is Clone Manager™ (by: Scientific and Educational Software™), alternatively programs are available via the internet: "ClustalW" for multiple alignments, and "Translate" for translations, both accessible at www.expasy.org; or the "Blast" programs at www.ncbi.nlm.nih.gov. Preferably the default scoring parameters are employed.

cDNA sequencing using primers SEQ ID NO: 28 and 29 was done for many isolates of the avian Astroviruses according to the invention. A selection of the resulting, trimmed nucleotide sequences are presented herein as in SEQ ID NO's: 4, 10, 12, 14, 16, 18, 20, 22, 24 and 26, as represented in Table 1.

These sequences were aligned to each other, using as reference the sequence of one isolate from a chicken, numbered 161319, to which the inventors refer as "isolate 19". Also, several DNA sequences of the corresponding parts of ORF 1a from other Astroviruses available in GenBank were aligned, for instance ANV1 (AB033998, SEQ ID NO: 1), turkey Astrovirus 1 (TAstV1) (Y15936), turkey Astrovirus 2

(AF206663), sheep Astrovirus (Y15937), mink Astrovirus (AY179509), and human astrovirus (Z25771); between hyphens are the respective GenBank accession numbers.

Of these other Astrovirus ORF 1a sequences, only ANV1, in particular the part of nt 2213-2607 from SEQ ID NO: 1, had a sequence identity that was significant, which means a nucleotide sequence identity percentage well above 50%. Of the remaining other Astroviruses, only TAstV1 (GenBank acc. nr: Y15936) had a detectable, but hardly significant sequence identity in the part of nucleotides nr. 2450-2856. This is represented in Table 2.

TABLE 2

List of percentage nucleotide sequence identity between SEQ ID NO: 4 (being a part of ORF 1a from isolate 19), and the sequence of the corresponding part of ORF 1a from other isolates of the avian Astrovirus according to the invention, as well as from other Astroviruses.

| Isolate/virus name | % nucleotide sequence identity to SEQ ID NO: 4 | SEQ ID NO, or GenBank accession no. |
| --- | --- | --- |
| 637 | 90 | SEQ ID NO: 10 |
| 686 | 88 | SEQ ID NO: 12 |
| 714 | 89 | SEQ ID NO: 14 |
| 715 | 98 | SEQ ID NO: 16 |
| 1736 | 89 | SEQ ID NO: 18 |
| 2383 | 88 | SEQ ID NO: 20 |
| 2388 | 88 | SEQ ID NO: 22 |
| 7279 | 89 | SEQ ID NO: 24 |
| 161317 | 89 | SEQ ID NO: 26 |
| ANV1 | 80 | SEQ ID NO: 1 (part: 2213-2607) GenBank: AB033998 |
| TAstV1 | 56 | GenBank: Y15936 (part: 2450-2856) |
| TAstV2 | <50 | GenBank: AF206663 (part: not detectable) |

A dendrographic tree of the results of these nucleotide sequence alignments is presented in FIG. 3.

Thus, it was surprisingly found that the group of novel avian Astroviruses according to the invention stand apart from all other Astroviruses, avian or mammalian, in that they share a nucleotide sequence identity of 88% or more when comparing a region of ORF 1a DNA sequences corresponding to SEQ ID NO: 4.

Therefore, in a preferred embodiment, the invention relates to the avian Astrovirus according to the invention, characterised in that the ORF 1a of said avian Astrovirus comprises a region having a nucleotide sequence identity of at least 88% with SEQ ID NO: 4.

More preferably, the invention relates to an avian Astrovirus according to the invention, characterised in that the ORF 1a of said avian Astrovirus comprises a region having a nucleotide sequence identity of at least 89% with SEQ ID NO: 4, even more preferably 90, 91, 92, 93, 94, 95, 96, 97, 98, 99, or 100% identity, in that order of preference.

Next to SEQ ID NO: 4, any one of the partial ORF 1a nucleotide sequences described in SEQ ID NO's: 10, 12, 14, 16, 18, 20, 22, 24 and 26, may serve to characterise the avian Astrovirus according to the invention in further preferred embodiments.

Analogous to the multiple alignment of the nucleotide sequences from ORF 1a as presented in Table 2, alignments can be made of the putative amino acid sequences from the trimmed nucleic acid sequences of Table 2, the SEQ ID NO's: 4, 10, 12, 14, 16, 18, 20, 22, 24 and 26. The resulting amino acid sequences—translated by computer—are presented herein as SEQ ID NO's: 5, 11, 13, 15, 17, 19, 21, 23, 25, and 27. The reference sequence is SEQ ID NO: 5, the putative amino acid sequence of part of ORF 1a of Isolate 19. The alignment was also made using the Align+ program, aligning over the full length of SEQ ID NO: 5. The results are presented in Table 3.

TABLE 3

List of percentage amino acid sequence identity between SEQ ID NO: 5 (being a translation of a part of ORF 1a from isolate 19), and the sequence of the corresponding part of ORF 1a from other isolates of the avian Astroviruses according to the invention, as well as from ANV1 and TAstV2.

| Isolate/virus name | % amino acid sequence identity to SEQ ID NO: 5 | SEQ ID NO, or GenBank accession no. |
| --- | --- | --- |
| 637 | 97 | SEQ ID NO: 11 |
| 686 | 97 | SEQ ID NO: 13 |
| 714 | 97 | SEQ ID NO: 15 |
| 715 | 99 | SEQ ID NO: 17 |
| 1736 | 96 | SEQ ID NO: 19 |
| 2383 | 94 | SEQ ID NO: 21 |
| 2388 | 93 | SEQ ID NO: 23 |
| 7279 | 96 | SEQ ID NO: 25 |
| 161317 | 97 | SEQ ID NO: 27 |
| ANV1 | 88 | GenBank: BAA92848 (part: 734-864) |
| TAstV2 | <40 | GenBank: Q9ILI6 (part: 810-930; hardly detectable) |

The detailed amino acid alignment is represented in FIG. 2.

The result of this amino acid sequence analysis, shows an outcome comparable to the results in Table 2: the amino acid sequences from the isolates of the avian Astrovirus according to the invention are more related amongst themselves, than when compared to other avian astroviruses. Identity percentages of the amino acid sequences of the various isolates of the avian Astrovirus according to the invention to SEQ ID NO: 5, are between 93 and 99%, while identity to ANV1 is less, at 88%.

Therefore, in a preferred embodiment, the invention relates to an avian Astrovirus according to the invention, characterised in that the ORF 1a of said avian Astrovirus encodes an amino acid sequence comprising a region having an amino acid sequence identity of at least 93% with SEQ ID NO: 5.

More preferably, the invention relates to an avian Astrovirus according to the invention, characterised in that the ORF 1a of said avian Astrovirus encodes an amino acid sequence comprising a region having an amino acid sequence identity of at least 94% with SEQ ID NO: 5, even more preferably 95, 96, 97, 98, 99, or 100% identity, in that order of preference.

Next to SEQ ID NO: 5, any one of the partial ORF 1a putatively translated nucleotide sequences described in SEQ ID NO's: 11, 13, 15, 17, 19, 21, 23, 25, and 27, may serve to characterise the avian Astrovirus according to the invention in further preferred embodiments.

In addition to nucleotide sequencing and alignment, the positive genetic marker of the avian Astroviruses according to the invention can be identified by using a PCR test to detect the presence of the 12 nucleotides in the ORF 1a region of the avian Astroviruses according to the invention, which are not present in the ORF 1a of ANV1, for instance in samples from birds suffering from intestinal or locomotory disease.

Therefore, in a further preferred embodiment, the avian Astrovirus according to the invention is characterised in that from the ORF 1a of said avian Astrovirus a PCR product of about 260 nucleotides can be produced in a PCR-assay using a set of the primers represented in SEQ ID NO's: 30 and 31.

The PCR primers to be used are:

```
SEQ ID NO: 30:
5'-GTY CTY ACC GAR GAR GAR TAY C-3'

SEQ ID NO: 31:
5'-AAD GTT ATY CTC CTA RGB TKH C-3'
```

The inventors refer to these primers as primers 29 and 30, respectively. These primers hybridise to nucleotides corresponding to ANV1 (SEQ ID NO: 1) nucleotide number 2252 and further, and to nucleotide number 2499 and proceeding in reverse.

The PCR product that was produced was visible on a gel as a band of about 260 nucleotides (this is including the length of the primers themselves). This band is produced only when the starting material contains DNA comprising the ORF 1a region of the avian Astroviruses according to the invention, as only these comprise the 12 nucleotides which are not present in ANV1 ORF 1a. A graphic representation of the specific binding of primers SEQ ID NO's: 30 and 31, in relation to the location of the 12 nucleotide region is presented in FIG. 4.

In such PCR assays the specificity and the sensitivity is determined by the specific PCR primers used, in particular by the primer's sequence and length. Optimisation of selectivity and sensitivity can then be achieved by adapting the reaction- and cycling conditions, such as the temperature and duration of the reaction steps, as is well known to a skilled person.

These, and other molecular biological techniques are explained in great detail in standard text-books like Sambrook & Russell: "Molecular cloning: a laboratory manual" (2001, Cold Spring Harbour Laboratory Press; ISBN: 0879695773); Ausubel et al., in: Current Protocols in Molecular Biology (J. Wiley and Sons Inc, NY, 2003, ISBN: 047150338X); C. Dieffenbach & G. Dveksler: "PCR primers: a laboratory manual" (CSHL Press, ISBN 0879696540); and "PCR protocols", by: J. Bartlett and D. Stirling (Humana press, ISBN: 0896036421).

Conveniently, the PCR reaction using the primers SEQ ID NO's: 30 and 31 is combined with, and directly follows the RT reaction required to produce cDNA; making the combined assay an RT-PCR assay, as described in the examples.

An RT-PCR assay as described, has been applied by the inventors on a variety of samples; a positive results was obtained with samples of the isolates of the novel avian Astrovirus according to the invention; a "positive" PCR result being the visualisation of an approximately 260 basepair reaction product after electrophoresis, in relation to appropriate positive and negative control samples. However, RT-PCR samples prepared from the related avian Astroviruses ANV1 and Chicken Astrovirus 2 (CAstV2) were consistently found to be negative in the PCR using the primers of SEQ ID NO's: 30 and 31.

An example of such a PCR test-result is represented in FIG. 5, showing a photograph of an Ethidium bromide stained, UV-light illuminated, agarose gel, on which PCR products were run of a PCR using primers SEQ ID NO's: 30 and 31. Only a sample of Isolate 19 reacted positive, samples containing ANV1 or CAstV2 were negative, as were negative controls.

Surprisingly, a highly remarkable and striking pathologic effect was observed upon infection and incubation of embryonated avian eggs with an avian Astrovirus according to the invention: affected embryo's displayed a bright-red staining of the legs and wing-tips. This has never been observed or described before. In addition, the infected embryo's displayed other, but less distinctive, features: a generalised light red staining, oedema of the abdomen, and a liver that was swollen considerably and had turned to a dark red/purple.

This specific pathology was observed about 2-7 days after infection of embryonated SPF chicken eggs, and almost always led to embryo mortality, depending on the virus titre that was inoculated.

For comparison, inoculation of ANV1 into embryonated eggs was done alongside, using similar test conditions. ANV1 did also induce swelling of the liver, but in that case the livers were even darker in color, and the overall color of the embryo was dark red. However, ANV1 never induced the specific bright red coloration of the legs and wing-tips that was seen for the isolates of the avian Astrovirus according to the invention.

Therefore, in a further preferred embodiment, the avian Astrovirus according to the invention is characterised in that it is capable of inducing a red coloration of the legs and wing-tips of chicken embryos, upon inoculation into embryonated chicken SPF eggs of about 5-7 days old, followed by incubation for 2-7 days, or even longer when appropriate.

As described, embryonated SPF chicken eggs and equipment for their incubation are available commercially. Typically, incubation of embryonated chicken eggs is done at about 35-39° C., in humidified atmosphere incubators.

Inoculation may be by any convenient route, e.g. the CAM, yolk sac or allantoic route.

As the skilled person will appreciate, the specific bright red coloration of legs and wing-tips may fail to become visible in incidental cases where e.g. the amount of virus that was inoculated is extremely low (not allowing "take" of the virus) or extremely high (causing mortality before coloration could occur); or where the embryo's are not of sufficient quality to allow viral replication. In general the specific bright red coloration can be observed upon inoculation of between about 10 and about 10^6 EID50/egg (EID50=egg infectious dose 50%)

One particular isolate of the avian Astroviruses according to the invention, named isolate 19, was further purified and amplified to serve as reference sample and be deposited. The isolate was purified by limiting dilution on chicken embryo liver (CEL) cells. Each time the highest dilution still inducing cpe on CEL cells was passaged on. Next this purified virus was amplified by three rounds of viral amplification in the allantoic cavity of embryonated SPF chicken eggs. Allantoic fluid was harvested and stored frozen. This purified virus was titrated on embryonated chicken SPF eggs, and was found to have a titer of 6.1 Log 10 EID50/ml. This was material was freeze dried in a standard stabiliser buffer and stored at −20° C. Sterility was confirmed. Samples of this virus material were then deposited at the "Collection Nationale de Cultures de Microorganismes" (CNCM) of the Institut Pasteur, 25 *Rue du Docteur Roux,* 75724 Paris *Cedex* 15, France, under deposit number: CNCM I-3895, on 23 Jan. 2008.

Therefore, in a further preferred embodiment, the avian Astrovirus according to the invention is a virus as deposited under number CNCM I-3895 at the Collection Nationale de Cultures de Microorganismes (CNCM), of the Institut Pasteur in Paris, France.

Although the sample that was purified, amplified, and deposited was the isolate named "isolate 19", however, either one of the isolates of the avian Astrovirus according to the invention, described in Table 1, can serve as reference sample for the novel group of avian Astroviruses according to the invention.

For in vitro culturing and for testing of the avian Astroviruses according to the invention, several culture systems can be used: e.g. (avian) cells lines, such as primary cells like CEL or chicken embryo kidney (CEK) cells, can advantageously be used. The preparation of CEL or CEK cell-cultures from embryonated chicken SPF eggs is well known to a person skilled in the art.

Especially CEK cells are well suited to monitor viral growth, and measure viral amount and viability. Even though the cytopathic effect (cpe) that the avian Astrovirus according to the invention produces on these cells is a-typical, infected cells can be clearly seen as rounded cells, curling up from the monolayer, and progression towards cell-lysis.

Therefore viral titration assays can be devised using progressive dilutions of viral samples, and scoring of the highest virus dilution still producing cpe. Viral titre can than be expressed as tissue culture infective dose 50% (TCID50) per mililiter as calculated by the Spearman-Kärber method (described in: D. Finney: Statistical method in biological assay, C. Griffin & Co., Londen, ISBN 0195205677). Such techniques are all well known to a skilled person.

This way the virus can be cultured in tissue culture flasks or microtitration plates for a variety of tests and purposes. Commonly it is beneficial to first adapt viruses isolated from the field to in vitro culture on cells, by applying a few passages on such cells, before use in virus tests or titrations.

Alternatively, tests and titrations can be performed in embryonated eggs, preferably chicken SPF eggs. For instance virus titration can be done by inoculation of increasingly diluted virus samples into the yolk sac of 6 day old embryonated SPF chicken eggs. After scoring the number of infected or dead embryos, the resulting titer of the sample tested can be expressed in EID50 per mililiter, for instance using the Spearman-Kärber method (supra).

For the deposited virus its capacity to cause pathology for hatched chickens and turkeys was confirmed under laboratory conditions in a number of experimental test chickens. Inoculation was via multiple routes: intramuscular, oral, and ocular. Several of the inoculated chickens developed severe signs of disease, whereas mock infected chickens were without symptoms. Symptoms observed were mortality, general depression, and mild to severe diarrhoea. Upon histopathology, nephritis and enteritis were observed. No disease of the legs or joints were observed, however that could also not expected as the chickens used for these experiments were too young (3-6 weeks), and/or not heavy enough (SPF chickens of layer type) to manifest such problems.

Of the deposited virus, the nucleotide sequence of additional regions of the genome is presented herein for further characterisation: ORF 1b and ORF 2. The respective nucleotide and putative amino acid sequences are presented herein as SEQ ID NO's: 5-8, see Table 1.

The different primers that were used to determine these additional nucleotide sequences are presented herein as SEQ ID NO's: 32-34, and are described in Table 4; for convenience this table also includes the other PCR- and sequencing primers described herein.

TABLE 4

Description of PCR-and sequencing primers as described herein

| SEQ ID NO: | Inventors' primer codes | Hybridises to: | Location of first base on SEQ ID NO: 1; direction | Sequence (5'→ 3') |
|---|---|---|---|---|
| RT reaction primer | | | | |
| 3 | 17 | 3' end-region of AAstV | 6731, rev | TCg WTS CTA CYC |
| Detection primers | | | | |
| 30 | 29 | Orf 1a of novel | 2252, fwd | gTY CTY ACC gAR gAR gAR TAY C |
| 31 | 30 | AAstV according to the invention | 2499, rev | AAD gTT ATY CTC CTA RgB TKH C |
| Sequencing primers | | | | |
| 28 | F-II | Orf 1a of | 2171, fwd | AAA ggK AAg ACD AAg ARR RAC Mg |
| 29 | R-II-3 | AAstV | 2640, rev | TCg CCT TCT ggA Agg TCT TCA |
| 32 | 20 | Orf 1b of | 3721, fwd | Tgg HCM CCY TTY TTY ggH g |
| 33 | 21 | AAstV | 4020, rev | RTT RTC MAC DgT KgT DgA RWA YTg |
| 34 | ORF2-R | Orf 2 of AAstV | 6622, rev | TTA gAT CTg AAA gCg CCg gAg g |

AAstV = avian Astrovirus;
rev = reverse;
fwd = forward

A further method to provide additional characterisation of the avian Astroviruses according to the invention, with the deposited virus sample as reference, is by determining its immunological features by serotyping, preferably by using VN- or IFT-assays.

In all tests, the novel avian Astrovirus proved to be immunologically disctinct from other avian viruses, as it could not be neutralised, and was not specifically bound by, antibodies specific for a variety of other avian viruses: Reovirus, Fowl Adenovirus (types 1, 2, 4, 5, and 8), Infectious Bronchitis virus, Newcastle Disease virus, Infectious Bursal Disease virus, avian Enterovirus (isolates 1821/9 and FP3), Egg drop syndrome and avian Influenza virus. This was also the case for antibodies specific for the avian Astroviruses ANV1 or CAstV2, whereas these sera did effectively neutralise their donor viruses: ANV1 and CAstV2 up to a 1:640 or a 1:10240 dilution respectively.

However, a sample of the deposited isolate 19 virus was effectively, and selectively neutralised by a chicken antiserum generated against isolate 19 in SPF chickens that were experimentally infected with the isolate 19 virus. After giving booster inoculations, a specific antiserum could be obtained. Read-out used for the virus neutralisation in this assay was the prevention of embryopathology by the neutralisation.

The results of the immunologic experiments wherein specific antibodies only recognised and neutralised the avian Astroviruses according to the invention, demonstrates that these viruses belong to a new and unique viral serotype.

This can be put to practice for instance in a further preferred embodiment, wherein the avian Astrovirus according to the invention is characterised in that said avian Astrovirus can be neutralised in a virus neutralisation assay, by antibodies directed against a sample of the Astrovirus as deposited under number CNCM I-3895 at the Collection Nationale de Cultures de Microorganismes (CNCM), of the Institut Pasteur in Paris, France.

An alternative approach to the generation of antibodies using the deposited virus according to the invention is also possible. For example, a virus-sample that is to be investigated for being (derived of) an avian Astrovirus according to the invention might itself be used to induce antibodies, which antibodies in turn can than be tested for their capacity to bind, or even to neutralise, an avian Astrovirus according to the invention. Conveniently such antibodies can be tested on a sample of the deposited virus according to the invention.

To this purpose, the test virus or a fraction or preparation thereof can be inoculated into an animal. The animal used for generation of such antibodies can in principle be any animal, but preferably a mouse, rat, rabbit, hamster, goat or chicken is used. Antibodies produced this way can be tested for binding or neutralisation to a avian Astrovirus according to the invention, e.g. conveniently by ordering a sample of the deposited virus according to the invention from the CNCM. This can be cultured, for instance on eggs, CEK or CEL cells, or other substrates, and finally incubated with the antibody raised with the test virus sample. Detection of antibody binding can be done e.g. by IFT or VN assay.

This thus constitutes a method for the identification and characterisation of a live or inactivated virus, or of a fraction or preparation thereof, as being or being derived from, an avian Astrovirus according to the invention.

Therefore, in a further preferred embodiment, the invention provides an avian Astrovirus according to the invention, which is characterised in that said virus is capable of inducing antibodies that can neutralise a sample of the deposited Astrovirus according to the invention in a VN assay.

Protocols for setting up a VN assays are well known in the art, and are within the routine capacity of a person skilled in the art. Preferences and details for VN assays are described above.

As is evident from the results of the immunologic assays using antibodies specific for the avian Astrovirus according to the invention, the invention also provides an antibody that can bind and that can neutralise an avian Astrovirus according to the invention.

Therefore, an other aspect of the invention is an antibody or fragment thereof that can neutralise the avian Astrovirus according to the invention, in a virus neutralisation assay.

Such antibodies according to the invention can be obtained and produced in a variety of ways, all well known and available to the skilled person. For instance the antibodies can be produced in experimental animals by (repeated) inoculation as described above.

Alternatively antibodies can be produced by immortalised B-lymphocyte cells, as in the hybrydoma technology. Modern improvements to the classic hybridoma technology have made this technique more efficient and productive, for instance by enhancing the amount of desired spleen cells before fusion, by positive selection (panning), followed by expansion in culture with a mixture of cytokines. Also the fusion-technique has been improved, by changing from the classic poly-ethylene glycol fusion, to electro-fusion.

In a further alternative approach, antibodies can be obtained through the use of molecular biological techniques and expression in recombinant expression systems. Molecular biological techniques allow the adaptation of such antibodies to better match the signature of antibodies from the target species that is to be treated, or the design of antibodies carrying two binding regions with different specificities. Expression system development allows the set up of high volume expression systems, such as expression in plants.

Recombinant expression systems are also well known in the art and for instance use: bacterial (e.g. *Escherichia coli, Salmonella, Bacillus, Caulobacter* etc.), yeast (e.g. *Saccharomyces*), insect (*Spodoptera, Trichoplusia*), mammalian (e.g. chinese hamster ovary), or plant (tobacco, potato, etc.) cells. These cells can be transformed with an expression construct carrying the heterologous sequence to be expressed. Also, combined systems are known, using a recombinant micro-organism comprising the nucleic acid to be expressed, which micro-organism can be cultured on cells in vitro to produce the desired protein at the desired scale. One example is the baculovirus/insect cell expression system. Finally, so-called cell-free expression systems are available commercially for cell-free expression of an appropriate recombinant DNA molecule.

The term "an antibody or fragment thereof" is meant to indicate that both complete immunoglobulin molecules or parts thereof are considered to be within the scope of the antibody according to the invention. Fragments of antibodies according to the invention are protein molecules that can still bind to an epitope of an avian Astrovirus according to the invention. Examples are FAB, scFv, Fv, dAb, or Fd fragments, all well known in the art.

Such fragments may be obtained from intact antibodies by e.g. chemical or enzymatic digestion. Alternatively such fragments can for example be obtained from a recombinant expression system, for example a phage-display system.

As is well known to a skilled person, the binding of an antibody or fragment thereof to a virus encompasses the recognition of epitopes on the virus particle. Most often these epitopes are formed by linear or three-dimensional conformations of molecules displayed on the viral particle. As a result, preparations of a virus or fractions thereof could be bound by antibodies or fragments thereof according to the invention, as long as these preparations or fractions still contain and present the right epitopes in the right form. In the case of the avian Astrovirus according to the invention the viral protein most prominently presented to the immune system is the capsid protein encoded from ORF 2.

The skilled person will also appreciate that when the antibody according to he invention was produced via inoculation of an animal, the animal serum obtained is a polyclonal antiserum, meaning that the antiserum contains a mixture of antibodies that can bind to a wide variety of epitopes. In practice this provides multiple interactions, which allow the efficient binding of preparations or fragments of the viral protein, even though these may not possess, or may not properly present, all of the epitopes that are normally available on an intact live virus particle.

Alternatively, the antibody according to the invention can be a monoclonal antibody, for instance as produced by the hybridoma technology, or the antibody according to the invention can be an antibody fragment such as a Fab fragment. In this case the antibody or fragment has a much reduced capacity to recognize different epitopes, as it will normally only bind specifically to a single epitope. Consequently when this particular epitope is not present or not displayed on the virus fragment or preparation, it may not be bound at all by such a monoclonal antibody or antibody fragment.

Antibodies according to the invention can be used in a variety of ways; for characterisation of the avian Astrovirus according to the invention, for diagnostics, for therapy, and/or for quality assurance purposes.

The invention provides the production of the avian Astrovirus according to the invention on an industrial scale. This can be achieved by culturing said virus on host cells in in vivo or in vitro systems. In vitro systems comprise primary or immortalised cell-lines. Examples of primary cells are CEK or CEL cells. An example of an immortalised cell-line is the LMH cell line (Kawaguchi et al., Cancer Res., vol. 47, p. 4460-4464). Examples of in vivo systems are culture in embryonated avian eggs, or in inoculated birds. Especially cultures on cells or eggs can be scaled up conveniently; e.g. cell cultures can be kept in containers of various sizes, such as flasks, roller bottles, or even fermentors. Techniques and equipment for cell-culture technology at any scale is well known and readily available from commercial suppliers.

Therefore the invention provides in a further aspect a host cell infected with an avian Astrovirus according to the invention.

Also, the invention provides a method of producing an avian Astrovirus according to the invention comprising multiplication of the avian Astrovirus according to the invention in an appropriate system, and harvesting the virus material.

The characterisations described herein of the avian Astrovirus according to the invention do not only refer to such avian Astroviruses in an intact, replication competent form. As a skilled person will appreciate, the present invention provides preparations of this virus in many different forms. These comprise for instance preparations wherein the avian Astrovirus according to the invention has been inactivated, or preparations wherein such a virus has been fractionated in one or more ways, (bio-)chemically or physically, for instance by extraction, lysation, digestion, homogenisation, or sonication.

Methods for inactivating virus are well known and for instance include chemical or physical inactivation, such as inactivation with formalin, beta-ethanolimine, or beta-propiolactone; also heating or irradiation with UV-light, X-rays, or radioactive radiation.

Methods for fractionation also are known in multitude, for instance extraction or lysation with a detergent such as Triton® X-100; digestion with trypsin; homogenisation by freeze-thawing or French cell-press; or sonication by ultrasound.

The starting material for such preparations can be a purified (live or inactivated) avian Astrovirus according to the invention, but also a host cell according to the invention, or a cell-culture or part thereof comprising a host cell or avian astrovirus according to the invention. For example such a part of a cell-culture may be a supernatant or a pellet of a centrifugated cell-culture. Evidently these cell-cultures or parts thereof may themselves be turned into preparations such as an extract, lysate, digest, homogenate, or sonicate as described.

Such preparations of the avian Astrovirus according to the invention contain one or more antigens and epitopes of the avian Astrovirus according to the invention.

Therefore in a further aspect, the invention relates to an antigenic preparation obtainable from the avian Astrovirus according to the invention.

The antigenic preparation according to the invention can be bound by antibodies or parts thereof according to the invention, or can itself be used to induce binding or neutralising antibodies or parts thereof. This can advantageously be applied in vaccines and diagnostics as will be described below.

Antigenic preparations according to the invention, are for example proteins from the avian Astrovirus according to the invention, or parts of such proteins. These proteins or parts thereof can be obtained by isolation from such a virus. However, these proteins or parts thereof can also conveniently be produced by recombinant DNA expression techniques using nucleic acids from the avian Astrovirus according to the invention. For instance nucleic acid sequences of part of the ORF 1a regions as described in any one of SEQ ID NO: 4, 10, 12, 14, 16, 18, 20, 22, 24 or 26 can be used; as described these cDNA sequences are related in that they have nucleotide sequence identity of at least 88% with SEQ ID NO: 4.

Therefore the invention provides in a further aspect a DNA molecule comprising a region having a nucleotide sequence identity of at least 88% with SEQ ID NO: 4.

Also nucleic acids of ORF 1b or ORF 2 can be used as described in SEQ ID NO: 6 or 8.

Such nucleic acid sequences and cDNA fragments can be cloned and expressed using recDNA techniques well known in the art, for instance by subcloning into a recombinant DNA molecule for further manipulation. The recDNA molecule can be a vector such as a bacterial plasmid. Preferably the nucleic acid from the avian Astrovirus according to the invention is operatively linked to an expression control sequence, such as a promoter, allowing its expression in an appropriate host cell or expression system. Alternatively the nucleic acid, cDNA, or recombinant DNA molecule can be introduced into a live recombinant carrier micro-organisms such as a bacterium or virus.

In analogy, based on the putative amino acid sequences described in SEQ ID NO's: 5, 11, 13, 15, 17, 19, 21, 23, 25, and 27, and their relatedness, the invention provides in a further aspect a protein comprising a region having an amino acid sequence identity of at least 93% with SEQ ID NO: 5.

These embodiments have great practical and advantageous utility in the application of vaccines and diagnostics as will be described below.

A vaccine can be prepared from live or inactivated microbiological pathogens, such as viruses, or from fragments of such micro-organisms. Such micro-organisms are commonly produced industrially in smaller or larger volumes, by incubation on cells, organs or tissues, embryonated eggs, or in host animals. After harvesting a suspension comprising the micro-organism, this suspension is formulated into a vaccine and the final product is packaged. After extensive testing for quality, quantity and sterility such vaccine products are released for sale.

The general techniques and considerations in vaccinology are well known in the art and are described for instance in governmental regulations and in handbooks such as: "Veterinary vaccinology" (P. Pastoret et al. ed., 1997, Elsevier, Amsterdam, ISBN: 0444819681), and: "Remington: the science and practice of pharmacy" (2000, Lippincot, USA, ISBN: 683306472).

A vaccine is commonly known in the art to represent a pharmaceutical composition comprising an immunogenic compound in a pharmaceutically acceptable carrier. The immunogenic compound is a live or inactivated micro-organisms, or a subunit thereof, capable of inducing an activation of a targets' immune system.

Surprisingly it was found that the avian Astrovirus according to the invention, and antigenic preparations, host cells, antibodies, nucleic acids, proteins, as well as methods for their preparation, culture, identification and quantification can be applied in vaccines and for diagnostic purposes. Such vaccines serve to protect a target animal from infection with the avian Astrovirus, or reduce the replication of said virus or the symptoms of the disease it causes. Such diagnostic assays allow the detection of the virus or its antigens e.g. in animal field samples or viral preparations.

Combined the vaccines and diagnostics allow the identification and defence against infection and/or disease by the avian Astrovirus according to the invention.

Vaccine capacity was demonstrated by the animal experiments described, in which chickens were inoculated with the avian Astrovirus according to the invention. This led to the production of highly specific antibodies. Moreover these antibodies were demonstrated to be able to neutralise specifically the avian Astrovirus according to the invention. As is well known in the art, the induction of neutralising antibodies is an important step in the feasibility of an effective and immunoprotective vaccine.

The repeated inoculations of the test animals not only provided a booster to the antibody levels produced, but also served as challenge infections, which could be tolerated and overcome by a large number of the birds in the test.

The avian Astrovirus according to the invention—or parts thereof—can thus be formulated in an appropriate pharmaceutical composition, and be applied to avians as a vaccine.

It is within reach of a skilled person to further optimise this vaccine, for instance by fine-tuning the efficacy and safety of the vaccine, so that it provides sufficient protection at an acceptable level of vaccination reaction. This can be done by adapting the vaccine dose, or by using the a vaccine in another form or formulation, or by adapting the other constituents of the vaccine (e.g. the stabiliser or the adjuvant), or by application via a different route.

Well known variants of a vaccine for the invention for instance may use the novel avian Astrovirus in a live or an inactivated form; may be a subunit vaccine when using the antigenic preparation and/or the protein according to the invention; may be in the form of a passive vaccine when using the antibody or fragment thereof according to the invention; or may be in the form of a DNA vaccine when using the DNA molecule according to the invention.

Therefore another aspect of the invention provides a vaccine comprising the avian Astrovirus, the antibody or fragment thereof, the antigenic preparation, the DNA molecule, or the protein all according to the invention, and a pharmaceutically acceptable carrier.

In analogy, the invention relates in further aspects to a compound or composition for use in a vaccine for poultry, wherein the compound or composition is the avian Astrovirus, the antibody or fragment thereof, the antigenic preparation, the DNA molecule, or the protein all according to the invention.

In a further aspect the invention relates to the use of a compound or composition for the manufacture of a vaccine for poultry, wherein the compound or composition is the avian Astrovirus, the antibody or fragment thereof, the antigenic preparation, the DNA molecule, or the protein all according to the invention.

In a further aspect the invention relates to a method for the manufacture of a vaccine for poultry, wherein a compound or composition is admixed with an appropriate pharmaceutical carrier, and wherein the compound or composition is the avian Astrovirus, the antibody or fragment thereof, the antigenic preparation, the DNA molecule, or the protein all according to the invention.

A "pharmaceutically acceptable carrier" can e.g. be sterile water, a physiological salt solution, or a buffer suitable for the purpose. In a more complex form the carrier may itself comprise other compounds, such as an adjuvant, an additional antigen, a cytokine, etc.

The vaccine according to the invention can be used both for prophylactic and for therapeutic treatment.

The term "vaccine" implies the presence of an immunologically effective amount of the avian Astrovirus according to the invention, and the presence of a pharmaceutically acceptable carrier.

What constitutes an "immunologically effective amount" for the vaccine according to the invention is dependent on the desired effect and on characteristics of the avian Astrovirus and the target organism. Determination of the effective amount is well within the skills of the routine practitioner, for instance by monitoring the immunological response following vaccination, or after a challenge infection, e.g. by monitoring the targets' clinical signs of disease, serological parameters, or by re-isolation of the pathogen, in comparison to the responses seen in unvaccinated animals.

The use of very high amounts of the avian Astrovirus, the antigenic preparation, the antibody or fragment thereof, the DNA molecule, or the protein according to the invention in a vaccine although immunologically very effective, will be less attractive for commercial reasons. A preferred amount of any of these compounds or compositions according to the invention, comprised in a vaccine according to the invention, is between 0.1 and 90% of the final volume of the vaccine. More preferably the amount is between 1 and 50%, 1 and 25%, and 1 and 10%, in that order of preference.

In case of an inactivated- or subunit vaccine, the compound or composition according to the invention can be expressed in ELISA units. Amounts of ELISA units that are effective need to be determined in relation to the Elisa unit of a standardised sample giving a certain efficacy.

In case of a live vaccine according to the invention, an amount of pfu (plaque forming units), cfu (colony forming units), TCID50, EID50, or EID50 (embryo lethal dose 50%) can be used, depending on what is a convenient way of quantifying the avian Astrovirus vaccine dose. For instance a live avian Astrovirus vaccine dose in a range between 1 and $10^{\wedge}6$ EID50 per vaccine dose can advantageously be used; preferably a range between 10 and $10^{\wedge}5$ EID50/dose, more preferably between $10^{\wedge}2$ and $10^{\wedge}4$ EID50/dose.

In a preferred embodiment the invention relates to the vaccine according to the invention wherein the avian Astrovirus according to the invention is in live form.

Live vaccines in general have the advantageous properties that only little inoculum is required, as the microorganism replicates itself. Also this generally induces a solid and effective immune response, with adequate immunological memory.

As known in the art, live vaccines can conveniently be applied as attenuated live vaccines, meaning the vaccine virus has a reduced virulence or pathogenicity compared to the original viral isolate. Methods for viral attenuation are known in the art and comprise for instance: continued passaging through animals or over cell-cultures; chemical attenuation; or attenuation by molecular biological techniques.

In an alternate preferred embodiment the invention relates to the vaccine according to the invention wherein the avian Astrovirus according to the invention is inactivated.

Methods and materials for viral inactivation have been described above. Such inactivated vaccines in general have the advantage of being more safe then live vaccines, as they do not expose the host to any potentially pathogenic replicating live avian Astrovirus.

In a further preferred embodiment, the vaccine according to the invention additionally comprises an adjuvant.

An adjuvant is an immunostimulatory substance boosting the immune response of the host in a non-specific manner. Many different adjuvants are known in the art. Examples of adjuvants frequently used are muramyldipeptides, lipopolysaccharides, several glucans or glycans, Carbopol®, Aluminum-hydroxide ($Al(OH)_3$). These can be combined with different emulsions, such as water in oil (w/o) emulsions, o/w emulsions and w/o/w double-emulsions. Oil adjuvants suitable for use in oily emulsions are e.g. mineral oils or metabolisable oils. Mineral oils are e.g. Bayol®, Marcol® and Drakeol®; metabolisable oils are e.g. vegetable oils, such as peanut oil and soybean oil, or animal oils such as the fish oil squalene. Alternatively a vitamin E (tocopherol) solubilisate as described in EP 382,271 may advantageously be used.

Very suitable o/w emulsions are e.g. obtained starting from 5-50% w/w water phase and 95-50% w/w oil adjuvant, more preferably 20-50% w/w water phase and 80-50% w/w oil adjuvant are used.

The amount of adjuvant added depends on the nature of the adjuvant itself, and on information with respect to such amounts provided by the manufacturer.

Whereas it is common practice to use adjuvants in combination with inactivated vaccines, several live vaccines have shown to also benefit from inclusion of an adjuvant. Therefore this embodiment is also within the scope of the invention.

In a further preferred embodiment the vaccine according to the invention additionally comprises a stabiliser.

A stabilizer can be added to the vaccine according to the invention e.g. to protect it from degradation, to enhance the shelf-life, or to improve freeze-drying efficiency. Useful stabilizers are i.a. SPGA (Bovarnik et al., 1950, J. Bacteriology, vol. 59, p. 509), skimmed milk, gelatine, bovine serum albumin, carbohydrates e.g. sorbitol, mannitol, trehalose, starch, sucrose, dextran or glucose, proteins such as albumin or casein or degradation products thereof, buffers, such as alkali metal phosphates, and polyamines such as spermine.

Also preservatives may be added, such as thimerosal, merthiolate, or gentamicin.

In addition, the vaccine may comprise one or more suitable surface-active compounds or emulsifiers, e.g. Span® or Tween®.

The vaccine may also comprise a so-called "vehicle". A vehicle is a compound to which the polypeptide or the protein according to the invention adheres, without being covalently bound to it. Such vehicles are i.a. bio-microcapsules, micro-alginates, liposomes and macrosols, all known in the art. A special form of such a vehicle is an immune stimulatory complex (ISCOM).

It goes without saying that admixing other stabilizers, carriers, diluents, emulsions, and the like to vaccines according to the invention are also within the scope of the invention. Such additives are described in well-known handbooks such as: "Remington", and "Veterinary Vaccinology" (both supra).

It is highly efficient to formulate the vaccine according to the invention as a combination-vaccine, as in this way multiple immunologic agents can be administered at once, providing reduction of time- and labour costs, as well as reduction of discomfort to the vaccinated target animals.

Such combination vaccines are achieved by combining the vaccine according to the invention with another antigenic compound, such as a (live or inactivated) virus, bacterium, parasite, or parts thereof such as a protein, a carbohydrate, or a nucleic acid capable of encoding an antigen. As the vaccine according to the invention is intended for avian target animals, it is advantageously combined with an additional antigen that is, or is derived from, an other poultry pathogen.

Therefore, in a further preferred embodiment, the vaccine according to the invention is comprising at least one additional antigen obtainable from a micro-organism pathogenic to poultry.

Many avian pathogens are known, however some of the more relevant veterinary-economic pathogens are:

viruses: infectious bronchitis virus, newcastle disease virus, avian influenza, Adenovirus, Egg drop syndrome virus, Infectious bursal disease virus (i.e. Gumborovirus), chicken aneamia virus, Avian encephalo-myelitis virus, Fowl Pox virus, turkey rhinotracheitis virus, Duck plague virus (Duck virus enteritis), Pigeon Pox virus, Marek's Disease, Avian Leucosis virus, Infectious laryngotracheitis virus, Avian pneumovirus, and Reovirus;

bacteria: *Escherichia coli, Salmonella* spec., *Ornitobacterium rhinitracheale, Haemophilis paragallinarum, Pasteurella multocida, Erysipelothrix rhusiopathiae, Erysipelas* spec., *Mycoplasma* spec. and *Clostridium* spec.;

parasites: *Eimeria;* fungi: e.g. *Aspergillus*, etc.

Also conceivable is the combination in the vaccine according to the invention of two or more avian Astroviruses according to the invention, for instance to form a combination vaccine that is more broadly effective against variants of the avian Astrovirus according to the invention. Examples of avian Astroviruses that may be used to form the combination vaccine are the isolates described in Table 1.

A vaccine according to the invention may take any form that is suitable for administration to poultry, and that matches the desired route of application and desired effect.

The preparation of a vaccine according to the invention is carried out by means well known to the skilled person. Preferably the vaccine according to the invention is formulated in a form suitable for injection, such as a suspension, solution, dispersion, emulsion, and the like. Commonly such vaccines are prepared sterile.

Many ways of administration can be applied, all known in the art. The vaccines according to the invention when inactivated, are preferably administered by injection; live vaccines, are preferably administered by a method of mass application such as via the feed, spray or drinking water.

The protocol for the administration of the vaccine according to the invention ideally is integrated into existing vaccination schedules of other vaccines.

Preferred target for the vaccine according to the invention is an avian animal. More preferred targets are selected from the group consisting of chicken, turkey, duck and goose. Most preferred target is chicken.

The dosing scheme for applying the vaccine according to the invention to a target organism can be in single or multiple doses, which may be given at the same time or sequentially, in a manner compatible with the formulation of the vaccine, and in such an amount as will be immunologically effective.

The age, weight, sex, immunological status, and other parameters of the avian target to be vaccinated is not critical, although it is evidently favourable to vaccinate healthy targets, and vaccinate as early as possible to prevent a field infection. For instance poultry can therefore be vaccinated at the day of hatching, or even earlier, while still in ovo at 3-4 days prior to hatch; for example at 18 days of embryonic development (ED) for chickens or at 24 days ED for turkeys.

For reasons of stability or economy a vaccine according to the invention may be freeze-dried. In general this will enable prolonged storage at temperatures above zero ° C., e.g. at 4° C. Procedures for freeze-drying are known to persons skilled in the art, and equipment for freeze-drying at different scales is available commercially.

Therefore, in a preferred embodiment, the vaccine according to the invention is in a freeze-dried form.

To reconstitute a freeze-dried vaccine composition, it is suspended in a physiologically acceptable diluent. Such a diluent can e.g. be as simple as sterile water, or a physiological salt solution such as (phosphate buffered) saline, or the diluent may already contain an adjuvating compound, such as a tochopherol, as described in EP 382,271. In a more complex form the freeze-dried vaccine may be suspended in an emulsion e.g. as described in EP 1,140,152.

Therefore in a further preferred embodiment, the invention relates to a vaccine composition obtainable by reconstitution of a freeze dried vaccine according to the invention.

In addition to the various uses of the compounds and compositions according to the invention in vaccines, these can also be advantageously applied in diagnostics, to detect the virus according to the invention or its antigens or nucleic acids e.g. in animal field samples or viral preparations.

This is also demonstrated by the results of the serotyping experiments by IFT and VN assay as described above, wherein antisera against the deposited avian Astrovirus according to the invention were applied to discriminate between viruses falling within the scope of the invention (the isolates as described in Table 1) and those that did not (amongst many others: ANV1, CAstV2, Reovirus etc.). Equally, the PCR experiments described demonstrated the capability to selectively identify the avian Astrovirus according to the invention.

As the skilled person will appreciate, this not only applies to the antibodies according to the invention, but also for the other compounds and compositions according to the invention. Such diagnostic assays for instance use the antibodies or fragments thereof according to the invention to test for antigen; or use antigen (the virus, the antigenic preparation, or the protein according to the invention) to test for antibodies thereagainst; or use nucleic acid (RNA from the virus, or the DNA molecule according to the invention) to set up hybridisation or PCR assays.

Therefore, in a further aspect, the invention relates to a diagnostic kit comprising the avian Astrovirus, the antigenic preparation, the antibody or fragment thereof, the DNA molecule, or the protein, all according to the invention.

The term "diagnostic kit" implies features relating to a package for commercial sale, for instance comprising a number of components and disposables for performing a diagnostic test and an instruction leaflet; all in a commercially feasible package form.

Such a diagnostic kit e.g. thus comprises the materials required for an antibody ELISA. In such a test for instance the wells of an ELISA plate have been coated with the avian Astrovirus according to the invention, to form an antibody ELISA kit, for the detection of antibodies against the avian Astrovirus according to the invention or preparations or proteins thereof. After incubation with the test-sample, labelled antibodies reactive with the immunoglobulins of the test sample (if present) are added to the wells. A colour reaction then reveals the presence in the test sample of specific antibodies.

Similarly, an antigen ELISA kit can be devised, comprising e.g. microtitration plates coated with the virus, the antigenic preparation, or the protein according to the invention.

The design of such immunoassays may vary. For example, the immunoassay may be based upon competition, in stead of on direct binding. Furthermore, such tests may also use particulate or cellular material, in stead of the solid support of a device. The detection of the antibody-antigen complex formed in the test may involve the use of labelled antibodies, wherein the labels may be, for example, enzymes or fluorescent-, chemo luminescent-, radio-active- or dye molecules.

Advantageously, the vaccines and diagnostics according to the invention can now be used in cooperation to devise an approach for the eradication of the avian Astrovirus according to the invention in a certain region or animal population.

LEGEND TO THE FIGURES

FIG. 1: displays a multiple alignment of the cDNA sequences of a section of ORF 1a from a selected number of isolates of the avian Astroviruses according to the invention. Reference is the sequence from Isolate 19. Outside reference is the corresponding part of the cDNA sequence of the genome of an ANV1 reference virus (SEQ ID NO: 1). The boxed area marks the 12 nucleotide region, which is not present in the ANV1 ORF 1a. Isolate 19-Orf 1a comprises the nucleotide sequence of SEQ ID NO: 4; 637-Orf 1a comprises the nucleotide sequence of SEQ ID NO: 10; 686-Orf 1a comprises the nucleotide sequence of SEQ ID NO: 12; 714-Orf 1a comprises the nucleotide sequence of SEQ ID NO: 14; 715-Orf 1a comprises the nucleotide sequence of SEQ ID NO: 16; 1736-Orf 1a comprises the nucleotide sequence of SEQ ID NO: 18, 2383-Orf 1a comprises the nucleotide sequence of SEQ ID NO: 20; 2388-Orf 1a comprises the nucleotide sequence of SEQ ID NO: 22; 7279-Orf 1a comprises the nucleotide sequence of SEQ ID NO: 24; and 161317-Orf 1a comprises the nucleotide sequence of SEQ ID NO: 26.

FIG. 2: displays a multiple alignment of the putative amino acid sequences, as prepared by computer translation of the cDNA sequences listed in FIG. 1. The boxed area marks the 4 amino acids, that are not present in the protein encoded by ORF 1a of ANV1. Isolate 19-Orf 1a comprises the amino acid sequence of SEQ ID NO: 5; 637-Orf 1a comprises the amino acid sequence of SEQ ID NO: 11; 686-Orf 1a comprises the amino acid sequence of SEQ ID NO: 13; 714-Orf 1a comprises the amino acid sequence of SEQ ID NO: 15; 715-Orf 1a comprises the amino acid sequence of SEQ ID NO: 17; 1736-Orf 1a comprises the amino acid sequence of SEQ ID NO: 19; 2383-Orf 1a comprises the amino acid sequence of SEQ ID NO: 21; 2388-Orf 1a comprises the amino acid sequence of SEQ ID NO: 23; 7279-Orf 1a comprises the amino acid sequence of SEQ ID NO: 25; and 161317-Orf 1a comprises the amino acid sequence of SEQ ID NO: 27.

FIG. 3: displays a dendrographic tree of the results of the nucleotide sequence alignments as presented in FIG. 1.

FIG. 4: presents a graphic representation of the hybridisation areas of primers SEQ ID NO's: 30 and 31, in relation to the location of the 12 nucleotide region (represented in bold) which is unique for the avian Astroviruses of the invention. Outside reference is the corresponding part of the cDNA sequence of the genome of an ANV1 reference virus (SEQ ID NO: 1). Isolate 19-Orf 1a comprises the nucleotide sequence of SEQ ID NO: 4.

Figure 5:
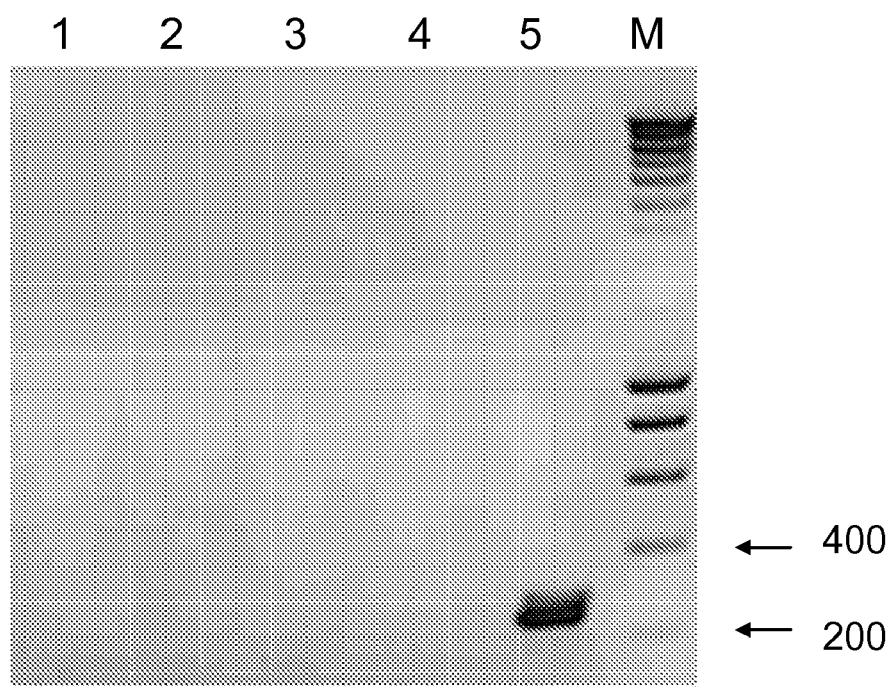

FIG. 5: shows a photograph of an Ethidium bromide stained, UV-light illuminated, agarose gel, on which the electrophoresis was run of the products of a PCR assay using primers SEQ ID NO's: 30 and 31 on a number of cDNA samples. The expected product of a positive PCR, a band of approximately 260 basepairs is clearly visible, in lane 5 only. The preceeding RT reactions had been done with the primer of SEQ ID NO: 3.

Lane 1: Negative control (no cDNA in PCR reaction)
Lane 2: Liverhomogenate from uninfected chicken
Lane 3: ANV1; a German isolate of 1991, amplified 1× CAM, 4× yolksac, allantoic fluid harvested.
Lane 4: CAstV2; derived from the virus as deposited at the CNCM under number CNCM I-2932, allantoic fluid.
Lane 5: Isolate 19 of the avian Astrovirus according to the invention, allantoic fluid
M: DNA size marker lane: bands at 200, 400, 600, 800, 1000 bp, etc.

The invention will now be further described with reference to the following, non-limiting, examples.

EXAMPLES

Example 1

Isolation of an Avian Astrovirus from Field Samples

Many isolates of avian Astrovirus according to the invention have been isolated from chickens and turkeys, from various farms in the Netherlands and Germany. As a typical example, the isolation of sample nr. 161319 ("Isolate 19") is described here in detail.

Isolate 19 Astrovirus was isolated from a pool of tracheas from 4 layer hens of 36 weeks old, on a Dutch farm, presenting a drop in feed consumption, drop in egg production and increase of second grade eggs. Also generally suffering from indigestion, diarrhea, and mobility problems.

Pooled tissue (0.5-1.0 g) of tracheas of the 4 birds were mixed with about 10 ml of "rinsing-medium" (containing: 500 ml HBSS [Hank's basic salt solution]+2 ml Benzyl Penicilline Natrium (1.000.000 I.E/ml)+8 ml Streptomycine (250 mg/ml)+0.5 ml Fungizone (2.000 μg/ml)+2 ml of $NaHCO_3$ 7.5%) and homogenised using a stomacher during 2 minutes. The suspension was centrifugated during 15 minutes at 2000×g at 2-8° C. The supernatant was then filtrated using a 450 nm filter.

The resulting fluid was inoculated into the allantoic cavity of four 8-9 day-embryonated chicken SPF eggs (1 ml per egg), the yolk of four 5-6 day-embryonated SPF eggs (1 ml per egg), and the CAM of four 9 day-embryonated SPF eggs (0.5 ml per egg) and incubated at 36.5 to 38.5° C. in 40 to 55% humidity. The eggs were candled daily. Embryonic death occurring within one day of inoculation was considered to be non-specific.

The embryos of the yolk-sac inoculated eggs did not show any abnormalities at 7 days p.i. Yolk fluid was harvested nonetheless and used for a second passage.

Four ml of the harvested yolk fluid from the first passage (1 ml per egg) was mixed with 0.5 ml of "passage medium" (containing: HBSS 90 ml+2 ml Benzyl Penicilline Natrium (1.000.000 I.E/ml)+8 ml Streptomycine (250 mg/ml)+0.5 ml Fungizone (2.000 μg/ml)+2 ml of $NaHCO_3$ 7.5%). From this mixture 1 ml per egg was inoculated in the yolk of five 5 day-embryonated SPF eggs and incubated at 36.5 to 38.5° C. with 40 to 55% humidity. The eggs were candled daily.

On the sixth day after inoculation, one embryo had died and showed redness of the body. The allantoic fluid from this egg was tested for Reovirus in agar gel precipitation (AGP) assay; it was negative for Reovirus.

About 4 to 5 ml of yolk of this egg with the abnormal embryo was harvested and used for further passages, in the same way as the second passage.

In the third passage, on the fifth day after inoculation, three embryos had died and two of them showed redness of the body. The pooled allantoic fluid was negative in the AGP for Reovirus, and for Adenovirus type1.

In further passages the titer of the isolate increased, as embryo's died or showed symptoms earlier after inoculation. In the $6^{th}$ and $7^{th}$ passage the typical bright red staining of the legs and wingtips became apparent.

Consistently, allantoic fluid was negative in HA or AGP tests for IBDV, Reovirus, Adenovirus, NDV, AIV and IBV. Also a PCR assay for IBDV was negative.

Harvested CAM and allantoic fluids were stored frozen at −80° C., and used for further characterisation.

Example 2

Viral RNA Isolation

For isolation of the total viral RNA, a QIAamp® Viral RNA mini Kit (QiaGen™) was used, according to the manufacturer's instructions. In short: 140 μl virus-containing fluid, such as allantoic fluid, or a tissue- or embryo homogenate (typically in quantities between 5-50% w/v), was mixed with prior prepared extraction buffer and carrier RNA. This was incubated at room temperature for 10 minutes. Next pure ethanol (96-100%) was added, mixed, and the mixture was applied to QIAamp Mini spin column (in a 2 ml collection tube). This was centrifuged for 1 min. at 6000×g. The flow-through was discarded. The column was washed with wash buffer containing pure ethanol. Finally, the column was eluted with 60 μl elution buffer. Commonly the RNA isolation was followed directly by production of cDNA via RT reaction.

Presence of Astroviral RNA was verified by standard agarose/formamide RNA gel-elektrophoresis.

Example 3

Production of cDNA Via RT Reaction

First strand cDNA synthesis was done using Amersham-Pharmacia™ Ready-To-Go® You-Prime First-Strand Beads, according to the manufacturer's instructions. In short: 29 μl of the eluted RNA from the total viral RNA isolation, was denatured for 10 minutes at 65° C., and 2 minutes on ice. This was added to a tube containing two beads, and 4 μl of 10 μM primer 17 (SEQ ID NO: 3) was added, to an endvolume of 33 μl. This was incubated for 1 minute at room-temperature, mixed by careful pipetting, and incubated for 1 hour at 37° C. cDNA was stored frozen below −20° C. until further use.

Example 4

PCR Reactions

PCR was used to prepare double stranded (ds) DNA from cDNA out of the RT reaction. Also PCR was used as a diagnostic type detection assay to identify specifically if avian Astrovirus according to the invention was present in a sample.

PCR reaction ingredients were from HT Biotechnolgy™ Ltd.: Supertaq® buffer (10× conc.) used at 1× conc.; Supertaq® Plus polymerase enzyme (5 U/μl) used at 1 U/μl, and preMixed dNTP's (10 mM), used at 2 mM. These were mixed in distilled, RNAse-free water.

Primers used were those as listed in Table 4. Primers were synthesised by Invitrogen™, the Netherlands, and the primer stock solution was made in TE buffer (pH 8.0) at 100 μM; the working-stock solution was at 10 μM dilution for direct use.

For a standard PCR, the following ingredients were used: 27 μl Aqua dest., 5 μl 10× Supertaq Plus buffer; 1 μl (equals 1 Unit) Supertaq Plus enzyme; 5 μl 2 Mm dNTP mixture; 5 μl each of forward and of reverse primer (at 10 μM); and finally 2 μl of cDNA from the RT reaction mixture; reaching a total volume of 50 μl.

Typical reaction conditions, for instance for amplifying ORF 1a with primers F-II and R-II-3 (SEQ ID NO: 28, 29), or ORF 1b by using primers 20 and 21 (SEQ ID NO: 32, 33) were:
1 min. at 95° C.,
40 cycles of: 30 sec. at 94° C.; 1 min. at 48° C.; and 40 sec. at 72° C.,
10 min. at 72° C.
hold at 20° C.
NB: all PCR temperatures are ±about 1° C.

During optimisations, some variations were applied: 45 instead of 40 cycles, and variations to the annealing temperature and -time in the cycling step: temperatures between 46 and 53° C. were used, at durations of 30 sec or 1 minute.

For the specific detection of the avian Astrovirus according to the invention, using primers 29 and 30 (SEQ ID NO: 30, 31) the optimal conditions used for the cycling phase were: 45 cycles, with an annealing step of 30 sec. at 51° C. Other conditions were as for the primers 20/21 reaction.

The PCR reactions for the cycle sequencing reactions had an essentially different set-up: 25 cycles of: 10 sec. at 96° C.; 5 sec. at 50° C.; and 2 min. at 60° C., see below.

Example 5

DNA Analysis by Aqarose Gel-Electrophoresis, Purification and Subcloning

Agarose gel-electrophoresis was used for detection and visualisation of the PCR products produced. Also this served to purify PCR products by excision and extraction, allowing the sequencing, or subcloning of these isolated PCR products.

In short, 0.8% Agarose (low electro-endosmosis type) gels were cast in TAE buffer (pH 8.0), containing about 50 μl of an 0.5 mg/ml solution of Ethidium-Bromide per 100 ml agarose solution. A sample of the PCR product was mixed 1:10 with standard sample loading buffer (glycerol/SDS//bromophenol blue). Typically a marker lane was included using SmartLadder® from Eurogentec™. Electrophoresis, submerged in TAE buffer, was performed typically for 1 hour at 100 V for a 20×20×1 cm gel, or until the blue dye reached the end of the agar. Visualisation was by UV light. Gels were photographed with a digital camera.

Agar gel electrophoresis was also used to estimate the DNA concentration of an excised and purified band; in that case a sample was run alongside to a number of lanes holding different quantities of the DNA marker ladder.

The purification of specific bands of PCR products from an agarose gel was done using the QIAquick® Gel Extraction kit (QiaGen™) according to the manufacturer's instructions, using either a micro-centrifuge or the QIAvac® vacuum manifold.

DNA bands excised and purified from agarose gel were subcloned into bacterial plasmids for further use, such as cloning, sequencing, expression, or hybridisation-detection assays. DNA fragments were cloned into plasmid pCR2.1 using a TOPO-TA® vector and TOPO-TA® cloning kit (Invitrogen™), according to the manufacturer's instructions Example 6

DNA Sequencing

DNA sequencing was performed by standard PCR cycle-sequencing, using a Big Dye® Terminator Ready Reaction Mix (ABI Prism™), and an ABI Prism™ 310 automated sequencing apparatus, all according to the manufacturer's instructions.

Typically 20 to 70 ng of DNA (purified PCR product, or cloned fragment in vector) were used in a sequencing reaction, with 8 μl Big Dye® Terminator Ready Reaction Mixture, 1 μl of 10 μM primer, in distilled water to a total volume of 20 μl. The primers used for sequencing were usually the same as those used in the PCR to prepare the ds DNA product from the cDNA.

Cycle sequencing PCR was by 25 cycles of: 10 sec. at 96° C., 5 sec. at 50° C., and 2 min at 60° C.

After PCR, the samples were purified using DyeEx® Spin columns (QiaGen™), for removal of Dye-Terminator, according to the manufacturer's instructions, using Eppendorf® tubes and a micro-centrifuge. The final eluate was resuspended 1:2 to a total volume of 40 μl with distilled water.

Sequence determination was then done by analysis on an ABI Prism® 310 Genetic Analyzer, with Data Collection version 1.0.4 en Sequence Analysis version 3 software.

Sequence analysis was done using a number of programs, most used were Sequencher® (Gene Codes™), and Clone Manager® (Sci. Ed. Software™). Start and end sequences were trimmed to remove nucleotide readings that were introduced based on the denatured PCR primers that were used.

The DNA sequences presented herein in SEQ ID NO's: 4-26 (even numbers), are the consensus sequences derived from multiple sequencing reactions. Most times the sequences were also read from both two strands, using forward and reverse sequencing primers; only SEQ ID NO: 8 was determined from only one strand. Average redundancy was about 4× per nucleotide.

Example 7

Titration of Astrovirus on Embryonated Chicken Eggs

Serial ten-fold dilutions of Astrovirus suspension were inoculated into the yolk sac of six-day-old embryonated SPF chicken eggs using a 23G 1" needle. Subsequently, the eggs were incubated for seven days at 37° C. in an egg incubator.

The eggs were candled daily. Mortality occurring within 24 hours post inoculation was considered non specific and therefore such eggs containing early dead embryos were discarded and excluded from the calculation of the infectivity titre.

Embryos dying from 2 till 7 days post inoculation were inspected for the presence of lesions characteristic for infection with the Astrovirus according to the invention; this was the case if the dead embryos exhibited bright red legs and wing-tips, and a swollen dark-red liver. The infectivity titre was calculated using a computer program based on the method of Spearman & Kärber and was expressed in EID50 per ml.

Example 8

Production of Astrovirus on Embryonated Chicken Eggs

Nine-day-old embryonated SPF chicken eggs were inoculated with $10^5$ EID50 of Astrovirus per egg in the yolk sac using a 22G 1½" needle. Subsequently, the eggs were incubated at 37° C. in an egg incubator.

After 24 hours of incubation the eggs were candled. Death occurring within 24 hours was considered non-specific, these eggs were removed.

After 48 hours of incubation the allantoic fluid of all remaining eggs was harvested. The allantoic fluid was stored frozen below −60° C.

The infectivity titre was established by titration in embryonated chicken eggs or on cells as described above.

Example 9

Production of Primary Cells

CEL cells were prepared from 14-16 day old embryonised SPF chicken eggs, by isolating the liver from the embryo. The liver was washed with PBS/phenol red, and incubated for 8-10 minutes at room temperature in a solution containing trypsin in PBS. Supernatant is harvested through a 100 µm gauze. This is repeated two more times, next cell are collected by centrifugation and resuspended in a suitable rich culture medium containing 5% fetal calf serum (FCS).

CEK cells were prepared in a similar way, using the kidneys from about 18 days old SPF chicken embryos. The kidneys were gently stripped, washed, and trypsinised once, for 20 minutes at room temperature. Next, CEK cells were filtered and taken up in culture medium+FCS.

Example 10

IFT Assay

Immunofluorescence tests (IFTs) were used to investigate the cross-species specificity of certain anti-sera, as well as for virus titration. Commonly IFT was performed on primary cells in microtitration plates.

When CEK cells were used for an IFT, these were seeded at $10^5$ cells/100 µl in the wells of 96-well microtitration plates. The cells were in a standard rich culturing medium, with 2% FCS and antibiotics, and incubated at 37° C. in 5% $CO_2$ atmosphere. The next day, virus was inoculated onto the cells.

For titration purposes, serial dilutions of virus were used. Plates were then incubated for a further 2 days. Then, supernatant was removed, and the cells were fixed with pure ethanol at −70° C. The plates could be stored at −20° C. until use. To visualise the virus for the titration, the plates were stained with specific antiserum. Therefore, the plates were adapted to room temperature, the alcohol was poured off and the plates were washed with PBS. A dilution of anti-Astrovirus serum was prepared at a strength which was known to give good fluorescence, but not too much background. This first antiserum was then brought onto the plates and incubated for 1 hours at 37° C. in a moist atmosphere. The plates were then washed 3× with PBS. Then the second antibody-conjugate was prepared, a goat anti-chicken IgG-FITC conjugate (Nordic™). This was brought onto the plates in the required dilution, and was incubated again for 1 hour at 37° C. After this incubation the plates were again washed 3× with PBS, after which a 1:1 mixture of PBS:glycerol was added. Plates were then stored in the dark at 4° C. until reading by fluorescence microscope. A positive signal is the detection of specific fluorescence, correlating to signs of cpe in the cell-layer.

For serum-characterisation, and species cross-reaction tests, micro-titration plates were prepared in a similar way, using CEK or CEL cells. Next day these were infected with the different viruses to be tested, e.g. Astrovirus isolates according to the invention, but also ANV1, and CAstV2, as well as other avian pathogens: Reovirus, IBV, NDV, FPV, Adenovirus, AIV, etc. The amount of virus was a fixed amount or a dilution whatever was convenient. The plates were incubated for 2-3 days.

To test the capacity of a certain antiserum to bind to different viruses, the serum was incubated on the plates, and signal was enhanced by incubation with conjugate. For optimisation of binding—versus—background signal, a number of dilutions of the antisera in PBS were tested on different dilutions of the various viruses.

Example 11

Infection of Chickens with Astrovirus

The avian Astrovirus according to the invention was tested in chickens in an experimental set-up to reproduce the disease symptoms observed in the field, and to re-isolate the microorganism from these secondary infected animals. This served to comply with Koch's postulates to establish the isolate tested as a pathogenic and virulent micro-organism and causative infectious agent of the field-symptoms observed.

Also, chickens were repeatedly infected to test vaccination efficacy by a live inoculum, against subsequent challenge infections.

Finally, total serum was isolated from experimentally infected chickens to obtain specific polyclonal antiserum against the inoculated Astrovirus.

To this purpose, SPF layer type chickens, of white leghorn breed and both sexes, were transferred to a negative pressure isolator at three weeks of age. Animals were assigned to treatment groups by random selection, and were individually labelled by double wing-bands. Standard food and drinking water were available ad libitum.

At regular intervals throughout the experiment blood samples were taken, also at day zero, to determine immune status. Next 15 chickens were inoculated by three routes: with 0.2 ml each by ocular and by intramuscular route, as well as with 0.5 ml by oral route, at $10^5$ EID50/0.2 ml dose, and $10^5.4$ EID50/0.5 ml dose. The inoculum was the isolate 19 Astrovirus as deposited, resuspended in water for injection. 5 chickens, placed in the same isolator were not inoculated to serve as controls, and sentinels. Animals were inspected daily for clinical signs of disease or mortality.

At day 20 post inoculation (p.i.), a number of chickens were bled and submitted for post-mortem histo-pathological examination. At day 23 p.i. the other (previously inoculated) chickens were boosted with a similar dose of inoculum. After another 23 days, the experiment was terminated, living animals were bled and examined.

Some birds were uninoculated initially but were housed in the same isolators as the inoculated/infected birds; as expected these birds became infected through horizontal spread of the Astrovirus.

Example 11a

Histopathology Results

The histopathological results of the animal trials were as follows: 2 chickens had died, and 5 animals, of which 3 controls had diarrhea. Upon histopathology several animals demonstrated more or less severe pathology to the kidney and intestinal tract already from day 7 p.i. The kidneys presented a severe interstitial nephritis, and tubular degeneration as most prominent signs. Thymus and bursa showed lymphocytolysis; the pancreas showed apoptosis and acinar atrophy; and the duodenum showed blunted and fused villi.

The horizontal infection of the uninoculated control chickens demonstrated the virulence and infectivity of the Astroviral inoculum.

Example 11b

PCR Results

Kidney samples of all chickens were tested by PCR for signs of the avian Astrovirus according to the invention. After homogenisation, and RNA isolation, RT samples were made. These were tested by PCR with primers of SEQ ID NO: 30 and 31. All samples of infected animals tested positive, by presenting the specific 260 by band identifying the avian Astrovirus according to the invention. Appropriate positive and negative controls were included.

This demonstrated that the causative agent of the mortality and histopathological signs was the avian Astrovirus according to the invention. The symptoms observed, nephritis and diarrhoea, concurred with those seen in the field. Problems to the leggs could not be reproduced; most likely the birds used where of too slender build to exhibit such problems, and/or the conditions of SPF chickens in an isolator did not sufficiently mimic the multiple infective pressure a bird in the field experienced.

Example 11c

VN Results

Fixed amounts of Astrovirus isolate 19 were incubated with chicken antisera from day 0, day 20 and day 46 p.i., for 1 hour at 37° C. These virus samples were then inoculated into 6 day old embryonated SPF eggs, and incubated for several days. At 4 days after egg-inoculation, embryo's receiving virus treated with day 0 serum had died, and showed typical signs of infection by the avian Astrovirus according to the infection.

However, virus incubated with serum taken at day 20, or day 46 serum had not affected the embryos. This demonstrates that isolate 19 virus can be effectively neutralised by a specific chicken antiserum.

Also this proves that effective antisera with VN capacity can be induced in chickens upon live inoculation with the avian Astrovirus according to the invention.

Example 11d

IFT Results

Results of cross-reaction IFT assays using the chicken polyclonal antisera demonstrated that an anti-Isolate 19 antiserum did not recognise any virus other than the virus isolates of the avian Astrovirus according to the invention.

Similarly, antisera specific for ANV1 or for CAstV2 equally only recognised the specific virus against which they had been raised. Equally important was that neither the anti-ANV1 nor the anti-ChAstV2 serum bound to a virus-isolate of the avian Astrovirus according to the invention. This applied even to the highest antibody amounts tested (the least diluted samples).

Also, none of the antisera against other avian pathogens, most relevantly Reovirus, could bind to the virus isolates of the avian Astrovirus according to the invention, or vice versa.

This demonstrated that the avian Astrovirus according to the invention is a novel and unique serogroup of its own, which thus confirmed the unique molecular biological differences identified.

Plates with CEK cells were infected with isolate 19 Astrovirus, $3^{rd}$ passage, in serial 10 fold dilutions of the virus. After two days, the plates were fixed and stained with different antisera:

anti isolate 19 serum-pool from day 33 post inoculation, 1:20 in PBS, anti ANV1 (strain SE-027/2), generated in chickens; 1:20 in PBS (the ANV1 is a German ANV1 isolate, which upon DNA sequencing of specific regions, appeared to be very closely related to the reference ANV 1 sequence from GenBank, that is used herein).

anti CAstV2 (strain TS9L), generated in chickens, 1:500 in PBS (the CAstV1 was derived from the sample that had been deposited at the CNCM in Paris, France, under deposit number I-2932).

negative control, only PBS.

After conjugation with goat anti-chicken IgG, the plates were read:

| | Virus | | | |
|---|---|---|---|---|
| Antiserum | Isolate 19 | ANV1 | CAstV2 | Negative CEK cells |
| anti Isolate 19 | Positive | Negative | Negative | Negative |
| anti ANV1 | Negative | Positive | Negative | Negative |
| anti CAstV2 | Negative | Negative | Positive | Negative |
| negative | Negative | Negative | Negative | Negative |

Example 12

Further Vaccination Trials

Inactivated Vaccine:

Turkeys and chickens will be vaccinated with an adjuvated vaccine of inactivated Astrovirus according to the invention, to optimise antigen dose.

Astrovirus isolate 19 was cultured on CEL as described, and is inactivated using beta-propiolactone (BPL) under control of temperature and pH, according to standard protocols. Inactivated Astrovirus is homogenised into a standard w/o emulsion consisting of a light mineral oil and appropriate emulsifiers, using standard protocols.

Turkeys and chickens will be housed in isolated units: 120 two-week-old conventional turkeys will be assigned to 6 separate groups (group 1-6) as they come to hand so that each group contains 20 animals. At three weeks of age, the turkeys in group 1-4 will be vaccinated by intramuscular route with the w/o emulsion vaccine, containing inactivated Astrovirus isolate 19. The turkeys in group 5 will be vaccinated by subcutaneous route with the same W/O emulsion vaccine and the turkeys in group 6 will not be vaccinated to serve as controls.

Similarly, 180 one-day-old SPF layer chickens will be assigned to 9 separate groups (group 7-15) as they come to hand so that each group contains 20 chickens. At three weeks of age the chickens in group 7-10 will be vaccinated by intramuscular route with a w/o emulsion vaccine, containing inactivated Astro type 3 virus. The chickens in group 11-14 will be vaccinated with the same vaccine by subcutaneous route and the chickens in group 15 will not be vaccinated to serve as controls.

Before the start of the experiment, and at 4, 8, and 12 weeks post-vaccination blood samples will be taken from all turkeys and chickens. The sera will be examined for the presence of antibodies specific for the Astrovirus according to the invention and their titers, by IFT on CEL cells, or by VN assay.

This protocol can easily be modified to include a duration of immunity study if relevant; e.g. by keeping the vaccinated birds in isolators for a further 6-12 months and then apply a challenge infection with an Astrovirus according to the infection.

Live Vaccine:

Chickens will be vaccinated with a dose of live Astrovirus according to the invention, and will subsequently be challenged with Astrovirus, to optimise the route of application for a live Astrovirus vaccine.

100 one-day-old commercial MDA+ (maternally derived antibody positive) breeder chickens will be assigned to 5 separate groups so that each group contains 20 chickens. At one day of age the chickens in group 1-4 will be vaccinated with live Astrovirus isolate 19 from allantoic fluid, via eye-drop, coarse spray, aerosol spray, or drinking water. The chickens in group 5 will not be inoculated to serve as unvaccinated controls. At 4 weeks post-vaccination all chickens will be challenged with an Astrovirus according to the invention. During three weeks after challenge all chickens will be observed daily for the occurrence of clinical signs characteristic for Astrovirus infection and/or mortality. Twenty-one days post-challenge all remaining chickens will be sacrificed, and submitted to histo-pathological examination.

The invention claimed is:

1. An isolated Avian Astrovirus having an open reading frame (ORF) 1a genomic region, characterised in that the ORF1a of said avian Astrovirus, when compared to the ORF 1a of avian nephritis virus 1, contains an insert of 12 nucleotides, said insert being located in between nucleotides corresponding to the nucleotides numbered 2485 and 2486 of SEQ ID NO: 1.

2. The isolated Avian Astrovirus according to claim 1, characterised in that the insert of 12 nucleotides has a nucleic acid sequence as presented in SEQ ID NO: 2.

3. The isolated Avian Astrovirus according to claim 1, characterised in that the ORF 1a of said avian Astrovirus comprises a region having a nucleotide sequence identity of at least 88% with SEQ ID NO: 4.

4. The isolated Avian Astrovirus according to claim 1, characterised in that from the ORF 1a of said avian Astrovirus a PCR product of about 260 nucleotides can be produced in a PCR-assay using a set of the primers represented in SEQ ID NO: 30 and SEQ ID NO: 31.

5. The isolated Avian Astrovirus according to claim 1, which is a virus as deposited under number CNCM I-3895 at the Collection Nationale de Cultures de Micro-organismes (CNCM), of the Institut Pasteur in Paris, France.

6. An isolated DNA molecule comprising a region having a nucleotide sequence identity of at least 88% with SEQ ID NO: 4.

7. An isolated protein comprising a region having an amino acid sequence identity of at least 93% with SEQ ID NO: 5.

8. A vaccine comprising the isolated avian Astrovirus according to claim 1 and a pharmaceutically acceptable carrier.

9. The vaccine according to claim 8, comprising at least one additional antigen obtainable from a micro-organism pathogenic to poultry.

10. An immunogenic composition for inducing an immune response in poultry, comprising the isolated avian Astrovirus according to claim 1.

11. A method for manufacturing a vaccine for poultry comprising mixing an appropriate pharmaceutical carrier and the isolated avian Astrovirus according to claim 1.

12. A diagnostic kit comprising the isolated avian Astrovirus according to claim 1.

13. A vaccine comprising the DNA molecule according to claim 6 and a pharmaceutically acceptable carrier.

14. A vaccine comprising the protein according to claim 7 and a pharmaceutically acceptable carrier.

* * * * *

SEQUENCE LISTING

<160> NUMBER OF SEQ ID NOS: 34

<210> SEQ ID NO 1
<211> LENGTH: 6927
<212> TYPE: DNA
<213> ORGANISM: Avian Nephritis Virus 1

<400> SEQUENCE: 1

```
ccgaatagat gggatggctt cggccggccc tactggggcg ggggctcgcc ccccaaaggc      60
tttcactgct caggccggac tggccaaatt ggtcaatccg gccggcttaa atagcatcct     120
cgctagaggg aaagaaaagt ttggaggcac ccaagcttgg aaagaactca tgggatgtga     180
tgttattttt gcaagatcca tcagtcactg gtatgggatt aaggggacga cttactatga     240
gcttactgtc gcactcggcc aacctctgta caaaccagtt acagatcctg aactgactga     300
agaggaaaag gccgtgatga ctgcagttca atctcggttt gcgcaaagta actctagtgt     360
tgttctcacc cgcacgctcc tgaataaaac ctgtgaactc aaggacagaa ttcgcgaact     420
tactgatgaa ttgggacaaa cagaagttca cctggcgcgt gaaaaagtga agcagcggc     480 cttgaagctt gagaatagaa aacttttttgt tgaaaatcag gaacttaaag accaacttga     540
gaaggagaga accaaacacg gctggaaggg cttgaaaaca ctgtgcctct ggatctttct     600
tgcgacatta attggtggtt acatcactgg ctctaacgca gcgtgtaccc ttgtcgatgt     660
tccatcccca atgaaagttg gttatgacac tttttaaacaa atgtgcatcc ataaggactc     720
ctatctacct gatggtgcct ttgacaaaga atctctggca cttgagtgtt ccaagcaaat     780
ggactatatg gattgcaaag aagttataac cgactcgatt tcagggaaga cttcctttgc     840
tggtatgctg cgtgatgttt ttagagtcga tgagattgtt actgctataa ggactgttgt     900
tcgctttgca atggacttca gtcttgcata cccaatttgt gtcatgttcg tgctcatctt     960
gaccagaaac aaaaaacatg caataatatc agcgtgttgt gcccttgttg ccaagtgttg    1020
tggattaaga cttttaccat tcactttagt tctcacttat gccccatctg aaacagctat    1080
agcaggttgt atttatggcc ttggctatat tagtatacca ttggtaacgt ttctccattg    1140
ggtcggtctt gtacttaagg ctattctcgt tcccgatgat tgctatatag gtactagggt    1200
gtcacatgca cttgcctggt ccataatgtt accaatgtgg attataacgc aagaacttat    1260
ggcatttaca gagtttcctc ttgaactcca aatagtcact accgtggttg tttgtacggc    1320
```

```
tggggttcggc ttccgttatc taactggtac ggttacgatt actgaaccag atggaaccgt    1380
aaagaagtac aagaggattt ttaatgccaa gagtgcaatt ggcactattt caacagtttt    1440
ttttgaaaaa gccaaggcca tacgtggggt gataccttcc ttcccaagta aggccgataa    1500
catcgtaaaa attgaggtag atgttgatgg tggttctgct ggagttggct ttagacttgg    1560
caactacatc tacacagcag gccatgttgt tggagaagca aaaatagcta aaatcacctg    1620
gaaaggctta acatctcaag ccaaggttct cggtcacatt gagttaccac tcttcacaga    1680
tacgcttgct cgtcttgaaa ttccaaaacc ttttcaacaa ctcccagtct ttagactagc    1740
aaagtcttct gagaacgact atgtgcagat ggtctgtttt gacaatcaat tgcaaaacgt    1800
tgtcactttc tcaggctggg ctaatattga cggcgattac ctgaatgctc ccttcgaaac    1860
ctatgcaggt acatcgggtt cacctattat aaatagggac gggaggatgc ttggtgtcca    1920
ttttggtagt aacgccgttg tgtcacaagg ttttgtgatc actaggcttt ttgcaactga    1980
gccagcggtt aagcagtgca agtctgatga agacctcgct gatgagattg ttcgtaaggt    2040
catgggcggt attaggattt cctttgcttc actcacatca gagctcgaga agcagcgcga    2100
tgaacttaac gcgctcaaac aaatggtcaa tgatcttata gacactgacc ttgttgccct    2160
cgagaagaag aaaggtaaga ctaagaggac cgttcgtggg cagaaacata gaccaaagc     2220
gatctctaag gctgccttca tgaaaactaa agtcctcacc gaagaagaat atcgccggtt    2280
agaggaggaa ggcttcacta agatgagat caaggacatc gttgacaatc tcagagagca    2340
ggcgtggctc gactatcaga accaacttga tgaagaaggt gatgatgact ggtacgaaca    2400
aatggaagag gatcaaagaa ttaatgatca aattgaccaa acattgaaa gagacctcga    2460
ggatagaggt gaatggtatg gtcagaggaa ataaccttc aagcaaagag cgatgcttcg    2520
tttcattcaa cttggccggc aacaacaggt ggccactgtc tcatttcctg atggttatga    2580
ggacagagct gaagaactct acaataaggt cgtcacaact gaagaccttc cagaaggcga    2640
aacttcagaa gcagcgctta gcctccccaa taaaattgtt catcaggcgg ggaagaggtt    2700
aaacttcaaa catgttaaga tacacccaga taagactttt atgaagtctg gtgttacaca    2760
aattgaagaa aagccagaag gtgatattat cctcaaagcc aaaacaacaa ctttggcccc    2820
taaggaagaa ccagtcatcc aacaggttga acaacaacct caagttgagc aacaacaaca    2880
acctcaacag cctgttgtgg aggagaagaa aagaacacca ccaccaaaac cacaaagaaa    2940
accaaagaca ggtgcaaaag cgaaatgcct cgattgtggc gagactttcg ttgaaaggca    3000
agacttccac gtttgtaagt caaaaaacta atgagcccc cttcggggg ctacacacct    3060
gtccctgacc atcttaggtg gaacaactgg caaatctata tggaacctct tgacttgaga    3120
ataacagtac ctgaaaacta tcctattctg ggtcatatcg ccatagataa attggttgaa    3180
cgtaagaaaa aggtcaatga cccgcttctc aaaatgcttg aacaaccaaa atgtgagggc    3240
tttacatcaa caacttggac tcgtaaagcg tacacaaaat ctttttgagaa gtttgactat    3300
ggcgatgcgg ttgattttgt gcaggactat cctgaactca ctgctttcgc agatgcagct    3360
gtacttgctg aggttggtta catggaggga acacatgtca ttcccatcca agaaaccagc    3420
aagaacatgg attctacacc tgcctttccc aaaatgcttg acttcgatag tgaaagggac    3480
tatctcgaag cacatgggat gaaagagtac attgatactc agttaggtgt gcaatctggc    3540
aaaccacttt ggtggtgctt cctttaaaaat gagatcctta aggaaaagaa agtcagtgaa    3600
gatgatatca ggattatcac ctgttcgac ccagtaataa ctaggctagg cgcctctttt    3660
gattcagaac aaaatgagcg catgaaggag agaacagaaa cgcatcatgc tcaggtgggc    3720
```

```
tggaccccct tctttggtgg actggataag cgtgtcagga gaattacgtc ctgtggcagg    3780
acccaagtcc tagaacttga ttggacgcga ttcgatggca ccattccggt tcagctcttc    3840
caaagaatgc gtgagctgcg taaattcttt ctcactaggc gttcaaggag gcgctatggc    3900
aagttacttg actggtacaa cgcccagtta acagatagaa tcactcttct tccaactgga    3960
gaggtaactc atgtcaagaa aggcaaccca tctgggcaat tttcaacaac agttgacaac    4020
aaccttgtta atgagtggtt gactgctttt gagtttggtt accaacactt ggagaaccat    4080
ggcattattc aacagtcaga gactaccgg gccaacgttg actttctttg ctatggagat    4140
gataggcttt tagcttttcaa tccatccttt gtcaactacg accctcaggt gaccattgat    4200
atgtataaaa atatctttgg gatgtgggtc aaacctgaaa acattaagct ctttgactcg    4260
ccaactggtt cttccttctg cggcttcact ttagttaagc cgcatgggca atgggtggga    4320
gtagttaatg tcaacaaact ccttcagagt cttaaaacac ccacgcgcag gctgccagac    4380
cttgaatccc tgtggggcaa gctcgtgtcg ctgaagatta tgtgctatca cagtgaccct    4440
gaggctgtgt cctacctttc caaccagata aggcgtgttg aagaatacgc tcgtgctgaa    4500
gggattgaac ttcctgaagt cgggcccgac ttctacagaa aaatctggtg agcggaggac    4560
caaaataact atggctggcg gtgccaccgc acctgcgggc gctaagccca agcaacctaa    4620
acagaagcag aaaaaaccat cttcacaggc aagaaagaag ccttcccaaa aacagaaggc    4680
aatgaaacca gtcaaacagg agttgaggaa ggttgaaaag caagtgagag tcctcaaggc    4740
gcgtacaaac ggacctaaag tcaatgacac aatgaagacc accgtaacag tgggcactct    4800
tgttggacaa acacaaagtg gattaaatcg ccaactcagg gtctcttta acccacttct    4860 tatgaagtcg acagaaggcg gtagcactac tccactctcc attcgtgcct caatgtacga    4920
gatgtggaaa ccactgagtg tggaaatttt tgccacgcca cttagtggct tctctagcgt    4980
ggtaggctca gttggtttta tggtcataac cttgaatgga cttgaggctt ccgcagattc    5040
aattgacacc ataaaagcca gaagacatgt ccagatggcg cttggcaggc cgtataggct    5100
taaactaagt gcccgtgaac ttgctggacc ccgtgaaggc tggtggctcg ttgacacttc    5160
tgaggcacct gccgatgcgt atgggcccagc tgttgatctc atgctggcat atgcaactga    5220
gaatctactt ggaacatctt ccggctccac aacttcctat acaggcacac tctggcaagt    5280
cgaaatgagg gttacctatg cattctccac ttacaaccca aaacctgggc tgcaaaccct    5340
tgtttcacag tccattactg gtggtcaaac tgtgaccatt caaccgtctc cggatgatgg    5400
gtcacttatt atgactacca atagccaaca agtcctagca ctcctaacac caggggtggc    5460
gggtcagagg aagggcaaat cccaaactat ttgggcaatt gccggctctg ctgtcgatgc    5520
cgctgccaca gtgcttggac catggggcta ccttctaaaa ggtggcttct ggcttgttcg    5580
actcatcttt ggtgggtcct ctgcaaggaa cacaacaaca aggcagtacc agatttatcc    5640
atcggtcgag tcagctttga ccgaccagcc aattttttggc aattctactg gtactcagag    5700
tgtcactgtg ccaatttgcc acatcactga agttgtgaac cccaatgcgg aaagtaacaa    5760 ccttcccccct ccaacgacag gagctcaacc tcaacctcaa cctcctgctc ctattgaaga    5820 atacttctg cctttagcag aactgactgg acaaccgggg gttccacctc tttatacttt    5880
tgatggcagt agctatacccc ccccaacaaa ctggctgggt tcaacaattc ttctcacagg    5940
aataccagct cacaagcgag ttactggaaa tctcgcaaaa tttggagtta ccaatctcca    6000
aatgtccaaa gttgcagcta ctgcacttga gatctatgac tttacagact ttggagtctt    6060
ctttggtacg ggaagctacc tctcggaggg gggaatacac actgggaaaa ccctgatcta    6120
```

-continued

```
ttcattaatg tctggccaaa caccaaatcc ttggctagca gcaaaccaat

```
act gaa gat caa aga att aat gat gag att gat aag caa att gag caa      240
Thr Glu Asp Gln Arg Ile Asn Asp Glu Ile Asp Lys Gln Ile Glu Gln
 65                  70                  75                  80 gac ctt gaa gat cga gga gaa tgg tat ggc cag tct ggg aaa cct agg      288
Asp Leu Glu Asp Arg Gly Glu Trp Tyr Gly Gln Ser Gly Lys Pro Arg
                 85                  90                  95 agg ata acc ttt aaa cag aga gcg atg ctt cgc ttc att cag ctt ggt      336
Arg Ile Thr Phe Lys Gln Arg Ala Met Leu Arg Phe Ile Gln Leu Gly
             100                 105                 110 cga caa caa caa ata gcc aca att tca ttt cct gat ggc tat gaa gat      384
Arg Gln Gln Gln Ile Ala Thr Ile Ser Phe Pro Asp Gly Tyr Glu Asp
         115                 120                 125 aga gct gaa gaa ctc tat aat aa                                       407
Arg Ala Glu Glu Leu Tyr Asn
     130                 135

<210> SEQ ID NO 5
<211> LENGTH: 135
<212> TYPE: PRT
<213> ORGANISM: novel avian Astrovirus - Isolate 19

<400> SEQUENCE: 5

Thr Lys Ser Ile Ser Lys Ala Ala Phe Met Lys Thr Lys Val Leu Thr
 1               5                  10                  15

Glu Glu Glu Tyr Arg Arg Leu Glu Glu Glu Gly Phe Ser Lys Asp Glu
                20                  25                  30

Ile Lys Glu Ile Val Asp Asn Leu Arg Glu Gln Ala Trp Ile Asp Tyr
             35                  40                  45

Gln Asn Gln Leu Asp Glu Glu Gly Asp Asp Asp Trp Tyr Glu Gln Met
         50                  55                  60

Thr Glu Asp Gln Arg Ile Asn Asp Glu Ile Asp Lys Gln Ile Glu Gln
 65                  70                  75                  80

Asp Leu Glu Asp Arg Gly Glu Trp Tyr Gly Gln Ser Gly Lys Pro Arg
                 85                  90                  95

Arg Ile Thr Phe Lys Gln Arg Ala Met Leu Arg Phe Ile Gln Leu Gly
             100                 105                 110

Arg Gln Gln Gln Ile Ala Thr Ile Ser Phe Pro Asp Gly Tyr Glu Asp
         115                 120                 125

Arg Ala Glu Glu Leu Tyr Asn
     130                 135

<210> SEQ ID NO 6
<211> LENGTH: 255
<212> TYPE: DNA
<213> ORGANISM: novel avian Astrovirus - Isolate 19
<220> FEATURE:
<221> NAME/KEY: CDS
<222> LOCATION: (1)..(255)

<400> SEQUENCE: 6 ctg gat aag cgt gtt agg aga atc act tcc tgt ggc agg acc caa gtc       48
Leu Asp Lys Arg Val Arg Arg Ile Thr Ser Cys Gly Arg Thr Gln Val
 1               5                  10                  15 tta gaa ctt gat tgg acg cgg ttc gac ggc acc att cca gtt cag ctc       96
Leu Glu Leu Asp Trp Thr Arg Phe Asp Gly Thr Ile Pro Val Gln Leu
                20                  25                  30 ttc caa aga atg cgt act atg cgt aaa ttc ttt cta act agg cgt tca      144
Phe Gln Arg Met Arg Thr Met Arg Lys Phe Phe Leu Thr Arg Arg Ser
             35                  40                  45
```

```
aga aag agg tat gga aaa cta ctt gac tgg tat aat gcc cag cta act      192
Arg Lys Arg Tyr Gly Lys Leu Leu Asp Trp Tyr Asn Ala Gln Leu Thr
         50                  55                  60 gat agg att act ctc tta cca aca gga gag gtg act cat gtc aag aag      240
Asp Arg Ile Thr Leu Leu Pro Thr Gly Glu Val Thr His Val Lys Lys
 65                  70                  75                  80 ggc aac cca tct gga                                                   255
Gly Asn Pro Ser Gly
                85

<210> SEQ ID NO 7
<211> LENGTH: 85
<212> TYPE: PRT
<213> ORGANISM: novel avian Astrovirus - Isolate 19

<400> SEQUENCE: 7

Leu Asp Lys Arg Val Arg Arg Ile Thr Ser Cys Gly Arg Thr Gln Val
 1               5                  10                  15

Leu Glu Leu Asp Trp Thr Arg Phe Asp Gly Thr Ile Pro Val Gln Leu
             20                  25                  30

Phe Gln Arg Met Arg Thr Met Arg Lys Phe Phe Leu Thr Arg Arg Ser
         35                  40                  45

Arg Lys Arg Tyr Gly Lys Leu Leu Asp Trp Tyr Asn Ala Gln Leu Thr
     50                  55                  60

Asp Arg Ile Thr Leu Leu Pro Thr Gly Glu Val Thr His Val Lys Lys
 65                  70                  75                  80

Gly Asn Pro Ser Gly
                85

<210> SEQ ID NO 8
<211> LENGTH: 380
<212> TYPE: DNA
<213> ORGANISM: novel avian Astrovirus - Isolate 19
<220> FEATURE:
<221> NAME/KEY: CDS
<222> LOCATION: (3)..(380)
<220> FEATURE:
<221> NAME/KEY: misc_feature
<222> LOCATION: (41)..(41)
<223> OTHER INFORMATION: n is a, c, g, or t

<400> SEQUENCE: 8 gg cct gac tgg act ggc ttc cct aaa ccg ggg gaa gga gan tac ttt       47
   Pro Asp Trp Thr Gly Phe Pro Lys Pro Gly Glu Gly Xaa Tyr Phe
    1               5                  10                  15 ctc caa atg caa gat aca act gat aga acg aca cat aca acg tgt gtt      95
Leu Gln Met Gln Asp Thr Thr Asp Arg Thr Thr His Thr Thr Cys Val
             20                  25                  30 agt atc tac att gtt gtt gct tat cgc cag tcg cgg agg ctg ata gcc     143
Ser Ile Tyr Ile Val Val Ala Tyr Arg Gln Ser Arg Arg Leu Ile Ala
         35                  40                  45 ttc ttt aac aat gca ggc cca gtc cgg gcg gcg ccc aca act atg ctt     191
Phe Phe Asn Asn Ala Gly Pro Val Arg Ala Ala Pro Thr Thr Met Leu
     50                  55                  60 tgt cta tac aat gtg gat gcg ggc cgg gca cca gct aca cca tac aat     239
Cys Leu Tyr Asn Val Asp Ala Gly Arg Ala Pro Ala Thr Pro Tyr Asn
 65                  70                  75 acc ttc caa ctc aca ctt caa agt gag ctt gct gac cca aat tct cca     287
Thr Phe Gln Leu Thr Leu Gln Ser Glu Leu Ala Asp Pro Asn Ser Pro
 80                  85                  90                  95 tct gat gat gaa gac gat gac atc tcg ctt gcg gga tca tgt ctt caa     335
Ser Asp Asp Glu Asp Asp Asp Ile Ser Leu Ala Gly Ser Cys Leu Gln
                100                 105                 110
```

```
gac gag ttt gat tgt gtg gat caa ctc gaa aaa gaa aga gaa gat         380
Asp Glu Phe Asp Cys Val Asp Gln Leu Glu Lys Glu Arg Glu Asp
                115                 120                 125
```

<210> SEQ ID NO 9
<211> LENGTH: 126
<212> TYPE: PRT
<213> ORGANISM: novel avian Astrovirus - Isolate 19
<220> FEATURE:
<221> NAME/KEY: misc_feature
<222> LOCATION: (13)..(13)
<223> OTHER INFORMATION: The 'Xaa' at location 13 stands for Glu, or
      Asp.

<400> SEQUENCE: 9

```
Pro Asp Trp Thr Gly Phe Pro Lys Pro Gly Glu Gly Xaa Tyr Phe Leu
1               5                   10                  15

Gln Met Gln Asp Thr Thr Asp Arg Thr Thr His Thr Thr Cys Val Ser
            20                  25                  30

Ile Tyr Ile Val Val Ala Tyr Arg Gln Ser Arg Arg Leu Ile Ala Phe
        35                  40                  45

Phe Asn Asn Ala Gly Pro Val Arg Ala Ala Pro Thr Thr Met Leu Cys
    50                  55                  60

Leu Tyr Asn Val Asp Ala Gly Arg Ala Pro Thr Pro Tyr Asn Thr
65                  70                  75                  80

Phe Gln Leu Thr Leu Gln Ser Glu Leu Ala Asp Pro Asn Ser Pro Ser
                85                  90                  95

Asp Asp Glu Asp Asp Ile Ser Leu Ala Gly Ser Cys Leu Gln Asp
                100                 105                 110

Glu Phe Asp Cys Val Asp Gln Leu Glu Lys Glu Arg Glu Asp
            115                 120                 125
```

<210> SEQ ID NO 10
<211> LENGTH: 407
<212> TYPE: DNA
<213> ORGANISM: novel avian Astrovirus - Isolate 637
<220> FEATURE:
<221> NAME/KEY: CDS
<222> LOCATION: (1)..(405)

<400> SEQUENCE: 10

```
act aaa tcg atc tca aaa gca gcc ttc atg aaa act aaa gtc ctc acc    48
Thr Lys Ser Ile Ser Lys Ala Ala Phe Met Lys Thr Lys Val Leu Thr
1               5                   10                  15 gaa gaa gaa tat cgt cgg ttg gag gag gaa ggc ttt tct aaa gat gag    96
Glu Glu Glu Tyr Arg Arg Leu Glu Glu Glu Gly Phe Ser Lys Asp Glu
            20                  25                  30 atc aaa gag att gtg gac aat ctt cgt gag cag gcc tgg att gat tat   144
Ile Lys Glu Ile Val Asp Asn Leu Arg Glu Gln Ala Trp Ile Asp Tyr
        35                  40                  45 cag aac caa ctt gat gaa gag ggt gat gat gac tgg tat gag caa atg   192
Gln Asn Gln Leu Asp Glu Glu Gly Asp Asp Asp Trp Tyr Glu Gln Met
    50                  55                  60 act gaa gat caa agg atc aat gat gaa att gac aag caa att gag caa   240
Thr Glu Asp Gln Arg Ile Asn Asp Glu Ile Asp Lys Gln Ile Glu Gln
65                  70                  75                  80 gac ctt gaa gat cga gga gat tgg tat ggc cag tct gga caa cct agg   288
Asp Leu Glu Asp Arg Gly Asp Trp Tyr Gly Gln Ser Gly Gln Pro Arg
                85                  90                  95 agg ata acc ttc aag caa agg gcg atg ctt cga ttc atc caa ctt ggt   336
Arg Ile Thr Phe Lys Gln Arg Ala Met Leu Arg Phe Ile Gln Leu Gly
                100                 105                 110
```

```
cga caa caa caa aca gcc aca att tca ttt cct gat ggc tat gaa gat    384
Arg Gln Gln Gln Thr Ala Thr Ile Ser Phe Pro Asp Gly Tyr Glu Asp
        115                 120                 125 aga gct gag gaa ctc ttt aat aa                                     407
Arg Ala Glu Glu Leu Phe Asn
    130             135

<210> SEQ ID NO 11
<211> LENGTH: 135
<212> TYPE: PRT
<213> ORGANISM: novel avian Astrovirus - Isolate 637

<400> SEQUENCE: 11

Thr Lys Ser Ile Ser Lys Ala Ala Phe Met Lys Thr Lys Val Leu Thr
1               5                   10                  15

Glu Glu Glu Tyr Arg Arg Leu Glu Glu Gly Phe Ser Lys Asp Glu
            20                  25                  30

Ile Lys Glu Ile Val Asp Asn Leu Arg Glu Gln Ala Trp Ile Asp Tyr
        35                  40                  45

Gln Asn Gln Leu Asp Glu Glu Gly Asp Asp Asp Trp Tyr Glu Gln Met
    50                  55                  60

Thr Glu Asp Gln Arg Ile Asn Asp Glu Ile Asp Lys Gln Ile Glu Gln
65                  70                  75                  80

Asp Leu Glu Asp Arg Gly Asp Trp Tyr Gly Gln Ser Gly Gln Pro Arg
                85                  90                  95

Arg Ile Thr Phe Lys Gln Arg Ala Met Leu Arg Phe Ile Gln Leu Gly
            100                 105                 110

Arg Gln Gln Gln Thr Ala Thr Ile Ser Phe Pro Asp Gly Tyr Glu Asp
        115                 120                 125

Arg Ala Glu Glu Leu Phe Asn
    130             135

<210> SEQ ID NO 12
<211> LENGTH: 407
<212> TYPE: DNA
<213> ORGANISM: novel avian Astrovirus - Isolate 686
<220> FEATURE:
<221> NAME/KEY: CDS
<222> LOCATION: (1)..(405)

<400> SEQUENCE: 12 act aaa tcg atc tca aaa gca gcc ttc atg aaa act aaa gtc ctc acc    48
Thr Lys Ser Ile Ser Lys Ala Ala Phe Met Lys Thr Lys Val Leu Thr
1               5                   10                  15 gaa gaa gag tat cgt cgg ttg gag gag gaa ggc ttt tct aaa gat gag    96
Glu Glu Glu Tyr Arg Arg Leu Glu Glu Glu Gly Phe Ser Lys Asp Glu
            20                  25                  30 atc aaa gag att gtg gac aat ctt cgt gag caa gct tgg att gac tat   144
Ile Lys Glu Ile Val Asp Asn Leu Arg Glu Gln Ala Trp Ile Asp Tyr
        35                  40                  45 cag aac caa ctt gat gaa gag ggt gac gat gac tgg tat gag caa atg   192
Gln Asn Gln Leu Asp Glu Glu Gly Asp Asp Asp Trp Tyr Glu Gln Met
    50                  55                  60 act gaa gat caa agg att aat gac gaa att gac aag cag atc gag caa   240
Thr Glu Asp Gln Arg Ile Asn Asp Glu Ile Asp Lys Gln Ile Glu Gln
65                  70                  75                  80 gat ctt gaa gac cga gga gat tgg tat ggc cag tct gga caa cct agg   288
Asp Leu Glu Asp Arg Gly Asp Trp Tyr Gly Gln Ser Gly Gln Pro Arg
                85                  90                  95 agg ata acc ttc aaa caa agg gcg atg ctt cgt ttc atc caa ctt ggt   336
```

```
Arg Ile Thr Phe Lys Gln Arg Ala Met Leu Arg Phe Ile Gln Leu Gly
            100                 105                 110 cgg caa caa caa aca gcc aca att tca ttt cct gat ggc tat gaa gat      384
Arg Gln Gln Gln Thr Ala Thr Ile Ser Phe Pro Asp Gly Tyr Glu Asp
        115                 120                 125 aga gct gag gag ctc ttt aac aa                                       407
Arg Ala Glu Glu Leu Phe Asn
    130                 135

<210> SEQ ID NO 13
<211> LENGTH: 135
<212> TYPE: PRT
<213> ORGANISM: novel avian Astrovirus - Isolate 686

<400> SEQUENCE: 13

Thr Lys Ser Ile Ser Lys Ala Ala Phe Met Lys Thr Lys Val Leu Thr
1               5                   10                  15

Glu Glu Glu Tyr Arg Arg Leu Glu Glu Gly Phe Ser Lys Asp Glu
            20                  25                  30

Ile Lys Glu Ile Val Asp Asn Leu Arg Glu Gln Ala Trp Ile Asp Tyr
        35                  40                  45

Gln Asn Gln Leu Asp Glu Glu Gly Asp Asp Asp Trp Tyr Glu Gln Met
    50                  55                  60

Thr Glu Asp Gln Arg Ile Asn Asp Glu Ile Lys Gln Ile Glu Gln
65                  70                  75                  80

Asp Leu Glu Asp Arg Gly Asp Trp Tyr Gly Gln Ser Gly Gln Pro Arg
                85                  90                  95

Arg Ile Thr Phe Lys Gln Arg Ala Met Leu Arg Phe Ile Gln Leu Gly
            100                 105                 110

Arg Gln Gln Gln Thr Ala Thr Ile Ser Phe Pro Asp Gly Tyr Glu Asp
        115                 120                 125

Arg Ala Glu Glu Leu Phe Asn
    130                 135

<210> SEQ ID NO 14
<211> LENGTH: 407
<212> TYPE: DNA
<213> ORGANISM: novel avian Astrovirus - Isolate 714
<220> FEATURE:
<221> NAME/KEY: CDS
<222> LOCATION: (1)..(405)

<400> SEQUENCE: 14 act aaa tcg atc tca aaa gca gcc ttc atg aaa act aaa gtc ctc acc       48
Thr Lys Ser Ile Ser Lys Ala Ala Phe Met Lys Thr Lys Val Leu Thr
1               5                   10                  15 gaa gag gaa tat cgt cgg tta gag gag gaa ggc ttt tcc aaa gat gag      96
Glu Glu Glu Tyr Arg Arg Leu Glu Glu Glu Gly Phe Ser Lys Asp Glu
            20                  25                  30 atc aaa gag att gtg gac aat ctt cgt gag cag gct tgg att gac tat     144
Ile Lys Glu Ile Val Asp Asn Leu Arg Glu Gln Ala Trp Ile Asp Tyr
        35                  40                  45 cag aac caa ctt gat gaa gag ggt gat gat gac tgg tat gaa caa atg     192
Gln Asn Gln Leu Asp Glu Glu Gly Asp Asp Asp Trp Tyr Glu Gln Met
    50                  55                  60 act gag gat caa agg atc aat gat gaa att gat aag caa att gag caa     240
Thr Glu Asp Gln Arg Ile Asn Asp Glu Ile Asp Lys Gln Ile Glu Gln
65                  70                  75                  80 gac ctt gaa gat cga gga gac tgg tat ggt cag tcc ggt caa cct agg     288
Asp Leu Glu Asp Arg Gly Asp Trp Tyr Gly Gln Ser Gly Gln Pro Arg
                85                  90                  95
```

```
agg ata acc ttc aag cag aga gct atg ctt cgc ttt atc caa ctt ggt      336
Arg Ile Thr Phe Lys Gln Arg Ala Met Leu Arg Phe Ile Gln Leu Gly
        100                 105                 110 cgg caa caa caa aca gcc aca att tca ttt cct gat ggc tat gaa gat      384
Arg Gln Gln Gln Thr Ala Thr Ile Ser Phe Pro Asp Gly Tyr Glu Asp
            115                 120                 125 aga gct gaa gag ctc tat aat aa                                       407
Arg Ala Glu Glu Leu Tyr Asn
    130                 135

<210> SEQ ID NO 15
<211> LENGTH: 135
<212> TYPE: PRT
<213> ORGANISM: novel avian Astrovirus - Isolate 714

<400> SEQUENCE: 15

Thr Lys Ser Ile Ser Lys Ala Ala Phe Met Lys Thr Lys Val Leu Thr
1               5                   10                  15

Glu Glu Glu Tyr Arg Arg Leu Glu Glu Glu Gly Phe Ser Lys Asp Glu
            20                  25                  30

Ile Lys Glu Ile Val Asp Asn Leu Arg Glu Gln Ala Trp Ile Asp Tyr
        35                  40                  45

Gln Asn Gln Leu Asp Glu Glu Gly Asp Asp Asp Trp Tyr Glu Gln Met
    50                  55                  60

Thr Glu Asp Gln Arg Ile Asn Asp Glu Ile Asp Lys Gln Ile Glu Gln
65                  70                  75                  80

Asp Leu Glu Asp Arg Gly Asp Trp Tyr Gly Ser Gly Gln Pro Arg
                85                  90                  95

Arg Ile Thr Phe Lys Gln Arg Ala Met Leu Arg Phe Ile Gln Leu Gly
        100                 105                 110

Arg Gln Gln Gln Thr Ala Thr Ile Ser Phe Pro Asp Gly Tyr Glu Asp
            115                 120                 125

Arg Ala Glu Glu Leu Tyr Asn
    130                 135

<210> SEQ ID NO 16
<211> LENGTH: 407
<212> TYPE: DNA
<213> ORGANISM: novel avian Astrovirus - Isolate 715
<220> FEATURE:
<221> NAME/KEY: CDS
<222> LOCATION: (1)..(405)

<400> SEQUENCE: 16 act aaa tcg atc tca aaa gct gcc ttc atg aaa aca aaa gtc ctt acc       48
Thr Lys Ser Ile Ser Lys Ala Ala Phe Met Lys Thr Lys Val Leu Thr
1               5                   10                  15 gaa gaa gaa tac cgt cgg tta gag gaa gaa ggc ttc tca aaa gat gag       96
Glu Glu Glu Tyr Arg Arg Leu Glu Glu Glu Gly Phe Ser Lys Asp Glu
            20                  25                  30 att aaa gag atc gtg gac aat ctg cga gaa caa gcc tgg atc gat tac      144
Ile Lys Glu Ile Val Asp Asn Leu Arg Glu Gln Ala Trp Ile Asp Tyr
        35                  40                  45 cag aat cag cta gat gaa gaa ggc gat gat gac tgg tat gag caa atg      192
Gln Asn Gln Leu Asp Glu Glu Gly Asp Asp Asp Trp Tyr Glu Gln Met
    50                  55                  60 act gaa gat caa aga atc aat gat gag att gat aag caa att gag caa      240
Thr Glu Asp Gln Arg Ile Asn Asp Glu Ile Asp Lys Gln Ile Glu Gln
65                  70                  75                  80 gac ctt gaa gat cga gga gaa tgg tat ggc cag tct ggg aaa tct agg      288
Asp Leu Glu Asp Arg Gly Glu Trp Tyr Gly Gln Ser Gly Lys Ser Arg
```

```
agg ata acc ttt aag cag aga gcg atg ctt cgg ttc att cag ctt ggt    336
Arg Ile Thr Phe Lys Gln Arg Ala Met Leu Arg Phe Ile Gln Leu Gly
            100                 105                 110 cga caa caa caa ata gcc aca att tca ttt cct gat ggc tat gaa gat    384
Arg Gln Gln Gln Ile Ala Thr Ile Ser Phe Pro Asp Gly Tyr Glu Asp
        115                 120                 125 aga gct gaa gaa ctc tat aat aa                                     407
Arg Ala Glu Glu Leu Tyr Asn
    130             135

<210> SEQ ID NO 17
<211> LENGTH: 135
<212> TYPE: PRT
<213> ORGANISM: novel avian Astrovirus - Isolate 715

<400> SEQUENCE: 17

Thr Lys Ser Ile Ser Lys Ala Ala Phe Met Lys Thr Lys Val Leu Thr
1               5                   10                  15

Glu Glu Glu Tyr Arg Arg Leu Glu Glu Glu Gly Phe Ser Lys Asp Glu
            20                  25                  30

Ile Lys Glu Ile Val Asp Asn Leu Arg Glu Gln Ala Trp Ile Asp Tyr
        35                  40                  45

Gln Asn Gln Leu Asp Glu Glu Gly Asp Asp Asp Trp Tyr Glu Gln Met
    50                  55                  60

Thr Glu Asp Gln Arg Ile Asn Asp Glu Ile Asp Lys Gln Ile Glu Gln
65                  70                  75                  80

Asp Leu Glu Asp Arg Gly Glu Trp Tyr Gly Gln Ser Gly Lys Ser Arg
                85                  90                  95

Arg Ile Thr Phe Lys Gln Arg Ala Met Leu Arg Phe Ile Gln Leu Gly
            100                 105                 110

Arg Gln Gln Gln Ile Ala Thr Ile Ser Phe Pro Asp Gly Tyr Glu Asp
        115                 120                 125

Arg Ala Glu Glu Leu Tyr Asn
    130             135

<210> SEQ ID NO 18
<211> LENGTH: 407
<212> TYPE: DNA
<213> ORGANISM: novel avian Astrovirus - Isolate 1736
<220> FEATURE:
<221> NAME/KEY: CDS
<222> LOCATION: (1)..(405)

<400> SEQUENCE: 18 acc aaa tcg atc tca aaa gca gcc ttc atg aaa act aaa gtt ctc acc    48
Thr Lys Ser Ile Ser Lys Ala Ala Phe Met Lys Thr Lys Val Leu Thr
1               5                   10                  15 gaa gaa gaa tat cgt cgg tta gag gag gaa ggc ttt tca aag gat gag    96
Glu Glu Glu Tyr Arg Arg Leu Glu Glu Glu Gly Phe Ser Lys Asp Glu
            20                  25                  30 atc aaa gag att gtg gac aat ctc cgt gaa caa gct tgg att gac tac    144
Ile Lys Glu Ile Val Asp Asn Leu Arg Glu Gln Ala Trp Ile Asp Tyr
        35                  40                  45 cag aac caa ctt gat gaa gaa ggt gat gat gac tgg tat gaa caa atg    192
Gln Asn Gln Leu Asp Glu Glu Gly Asp Asp Asp Trp Tyr Glu Gln Met
    50                  55                  60 act gaa gat caa agg atc aat gat gaa att gac aag cag att gaa caa    240
Thr Glu Asp Gln Arg Ile Asn Asp Glu Ile Asp Lys Gln Ile Glu Gln
65                  70                  75                  80
```

```
gat ctt gag gat cga gga gac tgg tat ggc cag tct ggt caa cct agg      288
Asp Leu Glu Asp Arg Gly Asp Trp Tyr Gly Gln Ser Gly Gln Pro Arg
            85                  90                  95 agg ata acc ttt aag cag aga gcg atg ctt cgc ttc att caa ctt ggg      336
Arg Ile Thr Phe Lys Gln Arg Ala Met Leu Arg Phe Ile Gln Leu Gly
        100                 105                 110 cga caa caa caa aca gct aca att tca ctt cct gat ggt tat gaa gat      384
Arg Gln Gln Gln Thr Ala Thr Ile Ser Leu Pro Asp Gly Tyr Glu Asp
            115                 120                 125 aga gct gaa gaa ctt ttt aac aa                                       407
Arg Ala Glu Glu Leu Phe Asn
        130             135

<210> SEQ ID NO 19
<211> LENGTH: 135
<212> TYPE: PRT
<213> ORGANISM: novel avian Astrovirus - Isolate 1736

<400> SEQUENCE: 19

Thr Lys Ser Ile Ser Lys Ala Ala Phe Met Lys Thr Lys Val Leu Thr
1               5                   10                  15

Glu Glu Glu Tyr Arg Arg Leu Glu Glu Gly Phe Ser Lys Asp Glu
            20                  25                  30

Ile Lys Glu Ile Val Asp Asn Leu Arg Glu Gln Ala Trp Ile Asp Tyr
        35                  40                  45

Gln Asn Gln Leu Asp Glu Glu Gly Asp Asp Asp Trp Tyr Glu Gln Met
    50                  55                  60

Thr Glu Asp Gln Arg Ile Asn Asp Glu Ile Asp Lys Gln Ile Glu Gln
65                  70                  75                  80

Asp Leu Glu Asp Arg Gly Asp Trp Tyr Gly Ser Gly Gln Pro Arg
            85                  90                  95

Arg Ile Thr Phe Lys Gln Arg Ala Met Leu Arg Phe Ile Gln Leu Gly
        100                 105                 110

Arg Gln Gln Gln Thr Ala Thr Ile Ser Leu Pro Asp Gly Tyr Glu Asp
            115                 120                 125

Arg Ala Glu Glu Leu Phe Asn
        130             135

<210> SEQ ID NO 20
<211> LENGTH: 407
<212> TYPE: DNA
<213> ORGANISM: novel avian Astrovirus - Isolate 2383
<220> FEATURE:
<221> NAME/KEY: CDS
<222> LOCATION: (1)..(405)

<400> SEQUENCE: 20 act aaa tcc atc tca aaa gca gcc ttc atg aaa act aaa gtt ctc acc       48
Thr Lys Ser Ile Ser Lys Ala Ala Phe Met Lys Thr Lys Val Leu Thr
1               5                   10                  15 gaa gaa gaa tat cgt cgg tta gag gag gaa ggc ttt tca aaa gat gag       96
Glu Glu Glu Tyr Arg Arg Leu Glu Glu Glu Gly Phe Ser Lys Asp Glu
            20                  25                  30 atc aaa gag att gtg gac aat ctc cgc gaa caa gcc tgg att gac tac      144
Ile Lys Glu Ile Val Asp Asn Leu Arg Glu Gln Ala Trp Ile Asp Tyr
        35                  40                  45 cag aac caa ctt gat gaa gaa ggt gat gat gac tgg tat gaa caa atg      192
Gln Asn Gln Leu Asp Glu Glu Gly Asp Asp Asp Trp Tyr Glu Gln Met
    50                  55                  60 act gaa gac caa aga gtc aat gat gaa att gat aag caa att gag cgg      240
```

-continued

```
Thr Glu Asp Gln Arg Val Asn Asp Glu Ile Asp Lys Gln Ile Glu Arg
 65                  70                  75                  80 gat ctt gaa gat cgt gga gag tgg tat ggt cag tct gga aaa ctt agg         288
Asp Leu Glu Asp Arg Gly Glu Trp Tyr Gly Gln Ser Gly Lys Leu Arg
                 85                  90                  95 aga ata acc ttc aag gaa aga gcg atg ctt cgc ttt att cag ctt ggt         336
Arg Ile Thr Phe Lys Glu Arg Ala Met Leu Arg Phe Ile Gln Leu Gly
             100                 105                 110 cga cag caa cat acg gcc act atc tca ttc cca gat ggt tat gaa gat         384
Arg Gln Gln His Thr Ala Thr Ile Ser Phe Pro Asp Gly Tyr Glu Asp
         115                 120                 125 aga gct gaa gaa ctc ttt aat aa                                          407
Arg Ala Glu Glu Leu Phe Asn
    130                 135

<210> SEQ ID NO 21
<211> LENGTH: 135
<212> TYPE: PRT
<213> ORGANISM: novel avian Astrovirus - Isolate 2383

<400> SEQUENCE: 21

Thr Lys Ser Ile Ser Lys Ala Ala Phe Met Lys Thr Lys Val Leu Thr
  1               5                  10                  15

Glu Glu Glu Tyr Arg Arg Leu Glu Glu Glu Gly Phe Ser Lys Asp Glu
                 20                  25                  30

Ile Lys Glu Ile Val Asp Asn Leu Arg Glu Gln Ala Trp Ile Asp Tyr
             35                  40                  45

Gln Asn Gln Leu Asp Glu Glu Gly Asp Asp Asp Trp Tyr Glu Gln Met
         50                  55                  60

Thr Glu Asp Gln Arg Val Asn Asp Glu Ile Asp Lys Gln Ile Glu Arg
 65                  70                  75                  80

Asp Leu Glu Asp Arg Gly Glu Trp Tyr Gly Gln Ser Gly Lys Leu Arg
                 85                  90                  95

Arg Ile Thr Phe Lys Glu Arg Ala Met Leu Arg Phe Ile Gln Leu Gly
             100                 105                 110

Arg Gln Gln His Thr Ala Thr Ile Ser Phe Pro Asp Gly Tyr Glu Asp
         115                 120                 125

Arg Ala Glu Glu Leu Phe Asn
    130                 135

<210> SEQ ID NO 22
<211> LENGTH: 413
<212> TYPE: DNA
<213> ORGANISM: novel avian Astrovirus - Isolate 2388
<220> FEATURE:
<221> NAME/KEY: CDS
<222> LOCATION: (1)..(411)

<400> SEQUENCE: 22 cat aaa act aaa tcg atc tct aag gct gcc ttc atg aaa aca aaa gtt          48
His Lys Thr Lys Ser Ile Ser Lys Ala Ala Phe Met Lys Thr Lys Val
  1               5                  10                  15 ctc acc gaa gaa gaa tat cgt cgg tta gag gag gaa ggc ttt tca aaa          96
Leu Thr Glu Glu Glu Tyr Arg Arg Leu Glu Glu Glu Gly Phe Ser Lys
                 20                  25                  30 gat gag atc aga gag att gtg gac aat ctc cgc gaa caa gct tgg att         144
Asp Glu Ile Arg Glu Ile Val Asp Asn Leu Arg Glu Gln Ala Trp Ile
             35                  40                  45 gac tac cag aat cag ctt gat gaa gaa ggt gat gac gac tgg tat gag         192
Asp Tyr Gln Asn Gln Leu Asp Glu Glu Gly Asp Asp Asp Trp Tyr Glu
         50                  55                  60
```

```
caa atg act gaa gat caa aga gtc aat gat gaa att gat agg caa att      240
Gln Met Thr Glu Asp Gln Arg Val Asn Asp Glu Ile Asp Arg Gln Ile
 65                  70                  75                  80 gag cag agt ctt gaa gat cgt ggc gac tgg tat ggc cag tct gga aag      288
Glu Gln Ser Leu Glu Asp Arg Gly Asp Trp Tyr Gly Gln Ser Gly Lys
                 85                  90                  95 cct agg aga ata acc ttc aag gaa aga gcg atg ctt cgc ttc att caa      336
Pro Arg Arg Ile Thr Phe Lys Glu Arg Ala Met Leu Arg Phe Ile Gln
            100                 105                 110 ctc ggg aga caa caa caa ata gcc aca att tca ttt ccc gat ggt tgt      384
Leu Gly Arg Gln Gln Gln Ile Ala Thr Ile Ser Phe Pro Asp Gly Cys
        115                 120                 125 gaa gat aga gct gaa gaa atc ttt aac aa                               413
Glu Asp Arg Ala Glu Glu Ile Phe Asn
    130                 135
```

<210> SEQ ID NO 23
<211> LENGTH: 137
<212> TYPE: PRT
<213> ORGANISM: novel avian Astrovirus - Isolate 2388

<400> SEQUENCE: 23

```
His Lys Thr Lys Ser Ile Ser Lys Ala Ala Phe Met Lys Thr Lys Val
 1               5                  10                  15

Leu Thr Glu Glu Glu Tyr Arg Arg Leu Glu Glu Glu Gly Phe Ser Lys
                 20                  25                  30

Asp Glu Ile Arg Glu Ile Val Asp Asn Leu Arg Glu Gln Ala Trp Ile
            35                  40                  45

Asp Tyr Gln Asn Gln Leu Asp Glu Glu Gly Asp Asp Asp Trp Tyr Glu
        50                  55                  60

Gln Met Thr Glu Asp Gln Arg Val Asn Asp Glu Ile Asp Arg Gln Ile
 65                  70                  75                  80

Glu Gln Ser Leu Glu Asp Arg Gly Asp Trp Tyr Gly Gln Ser Gly Lys
                 85                  90                  95

Pro Arg Arg Ile Thr Phe Lys Glu Arg Ala Met Leu Arg Phe Ile Gln
            100                 105                 110

Leu Gly Arg Gln Gln Gln Ile Ala Thr Ile Ser Phe Pro Asp Gly Cys
        115                 120                 125

Glu Asp Arg Ala Glu Glu Ile Phe Asn
    130                 135
```

<210> SEQ ID NO 24
<211> LENGTH: 407
<212> TYPE: DNA
<213> ORGANISM: novel avian Astrovirus - Isolate 7279
<220> FEATURE:
<221> NAME/KEY: CDS
<222> LOCATION: (1)..(405)

<400> SEQUENCE: 24

```
acc aaa gcg atc tcc aaa gct gcc ttc atg aaa act aaa gtt ctt acc       48
Thr Lys Ala Ile Ser Lys Ala Ala Phe Met Lys Thr Lys Val Leu Thr
 1               5                  10                  15 gaa gaa gaa tat cgt cgg tta gag gag gaa ggc ttt tct aaa gat gag       96
Glu Glu Glu Tyr Arg Arg Leu Glu Glu Glu Gly Phe Ser Lys Asp Glu
                 20                  25                  30 atc aaa gag att gtg gac aat ctt cgc gag cag gcc tgg att gat tac      144
Ile Lys Glu Ile Val Asp Asn Leu Arg Glu Gln Ala Trp Ile Asp Tyr
            35                  40                  45 cag aac caa ctt gat gaa gag ggt gat gat gac tgg tat gaa caa atg      192
```

```
                                                                         -continued Gln Asn Gln Leu Asp Glu Glu Gly Asp Asp Asp Trp Tyr Glu Gln Met
     50                  55                  60 act gaa gat caa agg atc aat gat gaa att gac aaa caa att gaa caa      240
Thr Glu Asp Gln Arg Ile Asn Asp Glu Ile Asp Lys Gln Ile Glu Gln
 65                  70                  75                  80 gat ctt gaa gat cga ggt gac tgg tat ggc cag tct ggt caa cct agg      288
Asp Leu Glu Asp Arg Gly Asp Trp Tyr Gly Gln Ser Gly Gln Pro Arg
                 85                  90                  95 agg ata act ttt aag cag agg gca atg ctt cgc ttc att cag ctc ggg      336
Arg Ile Thr Phe Lys Gln Arg Ala Met Leu Arg Phe Ile Gln Leu Gly
            100                 105                 110 cga caa caa caa acg gcc aca att tca ttt cct gat ggt tat gaa gat      384
Arg Gln Gln Gln Thr Ala Thr Ile Ser Phe Pro Asp Gly Tyr Glu Asp
        115                 120                 125 aga gct gaa gaa ctc ttc aac aa                                       407
Arg Ala Glu Glu Leu Phe Asn
    130                 135

<210> SEQ ID NO 25
<211> LENGTH: 135
<212> TYPE: PRT
<213> ORGANISM: novel avian Astrovirus - Isolate 7279

<400> SEQUENCE: 25

Thr Lys Ala Ile Ser Lys Ala Ala Phe Met Lys Thr Lys Val Leu Thr
 1               5                  10                  15

Glu Glu Glu Tyr Arg Arg Leu Glu Glu Glu Gly Phe Ser Lys Asp Glu
             20                  25                  30

Ile Lys Glu Ile Val Asp Asn Leu Arg Glu Gln Ala Trp Ile Asp Tyr
         35                  40                  45

Gln Asn Gln Leu Asp Glu Glu Gly Asp Asp Asp Trp Tyr Glu Gln Met
     50                  55                  60

Thr Glu Asp Gln Arg Ile Asn Asp Glu Ile Asp Lys Gln Ile Glu Gln
 65                  70                  75                  80

Asp Leu Glu Asp Arg Gly Asp Trp Tyr Gly Gln Ser Gly Gln Pro Arg
                 85                  90                  95

Arg Ile Thr Phe Lys Gln Arg Ala Met Leu Arg Phe Ile Gln Leu Gly
            100                 105                 110

Arg Gln Gln Gln Thr Ala Thr Ile Ser Phe Pro Asp Gly Tyr Glu Asp
        115                 120                 125

Arg Ala Glu Glu Leu Phe Asn
    130                 135

<210> SEQ ID NO 26
<211> LENGTH: 407
<212> TYPE: DNA
<213> ORGANISM: novel avian Astrovirus - Isolate 161317
<220> FEATURE:
<221> NAME/KEY: CDS
<222> LOCATION: (1)..(405)

<400> SEQUENCE: 26 act aaa tcg atc tca aaa gca gcc ttc atg aaa act aaa gtc ctc acc       48
Thr Lys Ser Ile Ser Lys Ala Ala Phe Met Lys Thr Lys Val Leu Thr
 1               5                  10                  15 gaa gaa gaa tat cgt cgg ttg gag gag gaa ggc ttt tct aaa gat gag       96
Glu Glu Glu Tyr Arg Arg Leu Glu Glu Glu Gly Phe Ser Lys Asp Glu
             20                  25                  30 atc aaa gag att gtg gac aat ctt cgt gag cag gcc tgg att gac tat      144
Ile Lys Glu Ile Val Asp Asn Leu Arg Glu Gln Ala Trp Ile Asp Tyr
         35                  40                  45
```

```
cag aac caa ctt gac gaa gag ggt gac gat gat tgg tat gag caa atg      192
Gln Asn Gln Leu Asp Glu Glu Gly Asp Asp Asp Trp Tyr Glu Gln Met
         50                  55                  60 act gaa gat caa agg atc aat gat gaa att gac aag caa att gag caa      240
Thr Glu Asp Gln Arg Ile Asn Asp Glu Ile Asp Lys Gln Ile Glu Gln
 65                  70                  75                  80 gac ctt gaa gat cga gga gat tgg tat ggc cag tct gga caa cct agg      288
Asp Leu Glu Asp Arg Gly Asp Trp Tyr Gly Gln Ser Gly Gln Pro Arg
                 85                  90                  95 agg ata acc ttc aag caa agg gcg atg ctt cga ttc atc caa ctt ggt      336
Arg Ile Thr Phe Lys Gln Arg Ala Met Leu Arg Phe Ile Gln Leu Gly
             100                 105                 110 cga caa caa caa aca gcc aca att tca ttt cct gat ggc tat gaa gat      384
Arg Gln Gln Gln Thr Ala Thr Ile Ser Phe Pro Asp Gly Tyr Glu Asp
         115                 120                 125 aga gct gag gaa ctc ttt aat aa                                        407
Arg Ala Glu Glu Leu Phe Asn
     130             135

<210> SEQ ID NO 27
<211> LENGTH: 135
<212> TYPE: PRT
<213> ORGANISM: novel avian Astrovirus - Isolate 161317

<400> SEQUENCE: 27

Thr Lys Ser Ile Ser Lys Ala Ala Phe Met Lys Thr Lys Val Leu Thr
 1               5                   10                  15

Glu Glu Glu Tyr Arg Arg Leu Glu Glu Glu Gly Phe Ser Lys Asp Glu
                 20                  25                  30

Ile Lys Glu Ile Val Asp Asn Leu Arg Glu Gln Ala Trp Ile Asp Tyr
             35                  40                  45

Gln Asn Gln Leu Asp Glu Glu Gly Asp Asp Asp Trp Tyr Glu Gln Met
         50                  55                  60

Thr Glu Asp Gln Arg Ile Asn Asp Glu Ile Asp Lys Gln Ile Glu Gln
 65                  70                  75                  80

Asp Leu Glu Asp Arg Gly Asp Trp Tyr Gly Gln Ser Gly Gln Pro Arg
                 85                  90                  95

Arg Ile Thr Phe Lys Gln Arg Ala Met Leu Arg Phe Ile Gln Leu Gly
             100                 105                 110

Arg Gln Gln Gln Thr Ala Thr Ile Ser Phe Pro Asp Gly Tyr Glu Asp
         115                 120                 125

Arg Ala Glu Glu Leu Phe Asn
     130             135

<210> SEQ ID NO 28
<211> LENGTH: 23
<212> TYPE: DNA
<213> ORGANISM: Artificial
<220> FEATURE:
<223> OTHER INFORMATION: Sequencing primer F-II for ORF1a fwd

<400> SEQUENCE: 28
aaaggkaaga cdaagarrra cmg                                             23

<210> SEQ ID NO 29
<211> LENGTH: 21
<212> TYPE: DNA
<213> ORGANISM: Artificial
<220> FEATURE:
<223> OTHER INFORMATION: Sequencing primer R-II-3 for ORF1a rev
```

```
<400> SEQUENCE: 29
tcgccttctg gaaggtcttc a                                              21

<210> SEQ ID NO 30
<211> LENGTH: 22
<212> TYPE: DNA
<213> ORGANISM: Artificial
<220> FEATURE:
<223> OTHER INFORMATION: PCR detection primer 29, fwd

<400> SEQUENCE: 30
gtyctyaccg argargarta yc                                             22

<210> SEQ ID NO 31
<211> LENGTH: 22
<212> TYPE: DNA
<213> ORGANISM: Artificial
<220> FEATURE:
<223> OTHER INFORMATION: PCR detection primer 30, rev

<400> SEQUENCE: 31
aadgttatyc tcctargbtk hc                                             22

<210> SEQ ID NO 32
<211> LENGTH: 19
<212> TYPE: DNA
<213> ORGANISM: Artificial
<220> FEATURE:
<223> OTHER INFORMATION: Sequencing primer 20, ORF1b fwd

<400> SEQUENCE: 32
tgghcmccyt tyttygghg                                                 19

<210> SEQ ID NO 33
<211> LENGTH: 24
<212> TYPE: DNA
<213> ORGANISM: Artificial
<220> FEATURE:
<223> OTHER INFORMATION: Sequencing primer 21, ORF1b rev

<400> SEQUENCE: 33
rttrtcmacd gtkgtdgarw aytg                                           24

<210> SEQ ID NO 34
<211> LENGTH: 22
<212> TYPE: DNA
<213> ORGANISM: Artificial
<220> FEATURE:
<223> OTHER INFORMATION: Sequencing primer ORF2-R

<400> SEQUENCE: 34
ttagatctga aagcgccgga gg                                             22
```